(12) United States Patent
Hanatsuka et al.

(10) Patent No.: US 9,046,457 B2
(45) Date of Patent: Jun. 2, 2015

(54) ROAD SURFACE CONDITION ESTIMATING METHOD, ROAD SURFACE CONDITION ESTIMATING TIRE, ROAD SURFACE CONDITION ESTIMATING APPARATUS, AND VEHICLE CONTROL APPARATUS

(75) Inventors: Yasushi Hanatsuka, Kodaira (JP); Hiroshi Morinaga, Kodaira (JP)

(73) Assignee: Kabushiki Kaisha Bridgestone, Tokyo (JP)

( * ) Notice: Subject to any disclaimer, the term of this patent is extended or adjusted under 35 U.S.C. 154(b) by 839 days.

(21) Appl. No.: 11/917,852

(22) PCT Filed: Jun. 19, 2006

(86) PCT No.: PCT/JP2006/312244
§ 371 (c)(1),
(2), (4) Date: Dec. 17, 2007

(87) PCT Pub. No.: WO2006/135090
PCT Pub. Date: Dec. 21, 2006

(65) Prior Publication Data
US 2009/0105921 A1      Apr. 23, 2009

(30) Foreign Application Priority Data
Jun. 17, 2005   (JP) ................................. 2005-178215

(51) Int. Cl.
 *B60T 8/00*        (2006.01)
 *G01N 19/02*       (2006.01)
 *B60G 17/0165*     (2006.01)
 *B60T 8/172*       (2006.01)
 *B60W 40/06*       (2012.01)

(52) U.S. Cl.
 CPC ............ *G01N 19/02* (2013.01); *B60G 17/0165* (2013.01); *B60G 2204/113* (2013.01);
(Continued)

(58) Field of Classification Search
 CPC  B60C 23/061; B60C 23/0408; B60C 23/062; B60T 2210/12; B60T 8/172
 USPC ............................................... 701/80; 73/146
 See application file for complete search history.

(56) References Cited

U.S. PATENT DOCUMENTS 2,612,928 A * 10/1952 Buddenhagen ............ 152/209.2
5,749,984 A   5/1998 Frey et al.
(Continued)

FOREIGN PATENT DOCUMENTS

DE    102004016288 B3    8/2005
EP     1 219 515 A1      7/2002
(Continued)

OTHER PUBLICATIONS

European Search Report dated Jul. 7, 2009.

*Primary Examiner* — Redhwan K Mawari
*Assistant Examiner* — Rodney P King
(74) *Attorney, Agent, or Firm* — Sughrue Mion, PLLC

(57) ABSTRACT

The vibration of a tire 10 of a running vehicle in the circumferential direction or the width direction is detected by a road surface condition estimating tire 10, provided with an acceleration sensor 11 and a signal processing unit 12. Data of a detected vibration waveform are divided into data of three domains, namely, a pre-leading domain, a contact patch domain, and a post-trailing domain, and then the vibration levels in the pre-leading domain and the contact patch domain, respectively, are extracted. At the same time, a vibration component in a low-frequency band and a vibration component in a high-frequency band are extracted respectively from the vibration levels in the respective domains, and respective vibration level ratios R, which are each a ratio thereof, are calculated. Then, on the vehicle body side, the condition of a road surface on which the vehicle is running is estimated, based on the calculated vibration level ratio R and a map 32M, stored in a storage means 32, showing a relationship between the vibration level ratio R of tire vibration and road surface conditions. Thus a road surface condition can be estimated with accuracy even when there are changes in temperature or vehicle speed.

3 Claims, 17 Drawing Sheets

(52) U.S. Cl.
CPC ..... *B60G2400/206* (2013.01); *B60G 2400/252* (2013.01); *B60G 2400/821* (2013.01); *B60G 2600/70* (2013.01); *B60G 2800/162* (2013.01); *B60G 2800/702* (2013.01); *B60G 2800/916* (2013.01); B60T 8/1725 (2013.01); *B60T 2210/12* (2013.01); B60W 40/06 (2013.01); *B60W 2422/70* (2013.01); *B60W 2550/147* (2013.01)

(56) References Cited

U.S. PATENT DOCUMENTS

2002/0162389 A1* 11/2002 Yokota et al. .................. 73/146
2005/0085987 A1  4/2005 Yokota et al.
2006/0260390 A1* 11/2006 Oflaz .............................. 73/146

FOREIGN PATENT DOCUMENTS

| | | |
|---|---|---|
| JP | 6-258196 A | 9/1994 |
| JP | 8-298613 A | 11/1996 |
| JP | 2002-511812 A | 4/2002 |
| JP | 2002-340863 A | 11/2002 |
| JP | 2003-182476 A | 7/2003 |
| JP | 2004-151910 A | 5/2004 |
| JP | 2005-59800 A | 3/2005 |
| JP | 2005-205956 A | 8/2005 |
| WO | 98/56606 A1 | 12/1998 |
| WO | 2006/034731 A1 | 4/2006 |

* cited by examiner

ROAD SURFACE CONDITION ESTIMATING METHOD, ROAD SURFACE CONDITION ESTIMATING TIRE, ROAD SURFACE CONDITION ESTIMATING APPARATUS, AND VEHICLE CONTROL APPARATUS

TECHNICAL FIELD

The present invention relates to a method for estimating the condition of a road surface on which a vehicle is running, a tire used in estimating a road surface condition, an apparatus for estimating a road surface condition based on information from the tire, and a vehicle control apparatus provided with the road surface condition estimating apparatus.

BACKGROUND ART

To increase the running stability of a vehicle, it is desired that the condition of a road surface on which a vehicle is running, or the coefficient of friction between tire and road surface (road surface friction coefficient), be estimated with accuracy and the estimated result fed back to vehicle control. In particular if the road surface condition, or the value of road surface friction coefficient, can be estimated before the driver initiates a danger-avoiding control, such as braking or steering, it will help enhance the accuracy of vehicle control technology, such as ABS (anti-braking system) and VSC (vehicle stability control), thus improving vehicular safety markedly.

As a conventionally proposed method for estimating a road surface friction coefficient, there is a technique for estimating a road surface condition, especially a maximum friction coefficient of a road surface, from a relationship between the change in slip ratio when the accelerator or brake is operated and the vehicle body acceleration. This method utilizes the correspondence between the measure of road surface friction coefficient μ and the vehicle body acceleration Ab. That is, the condition of a road surface when a vehicle is running is estimated by comparing a vehicle body acceleration with the predetermined Ab/S values for a vehicle running on a low μ road, an medium μ road, and a high μ road, within a stable domain of a "vehicle body acceleration Ab–wheel slip S" characteristic curve. By this method, the measure of road surface friction coefficient μ can be easily estimated from the vehicle body acceleration Ab (See Reference 1, for instance).

There is also a proposed method which utilizes the fact that the vibration level of a tire of a running vehicle changes with the road surface condition. According to the method, a vibration sensor or the like is attached to a tire and a road surface condition is estimated using the tire as a sensor. In this method, a vibration sensor is installed on the inner side of a tire tread, and the vibration level of the tire tread portion of a running vehicle is detected. Then after obtaining a vibration waveform of the vibration level arranged in a time series, a curve representing a vibration level distribution is prepared by correlating the vibration detecting positions to the time axis of the waveform and having the vertical axis represent the power value (OA, or oscillation amplitude, power value of vibration). Thus a road surface condition while a vehicle is running is estimated by comparing an OA power value of vibration in a tire contact patch domain of this vibration level distribution with a previously prepared master curve of vibration level distribution for the running of a vehicle on various kinds of road surfaces. This method enables accurate estimation of a road surface condition while the vehicle is running (See Reference 2, for instance).

Reference 1: Japanese Unexamined Patent Application Publication No. 7-112659
Reference 2: WO 01/098123 A1

DISCLOSURE OF THE INVENTION

Problems to be Solved by the Invention

In the above-mentioned method for estimating a road surface friction coefficient from the vehicle body acceleration, however, the road surface friction coefficient can be estimated only when the driver executes a certain control, such as acceleration or deceleration, and it is impossible to estimate a road surface friction coefficient during a normal running of a vehicle. Hence, the method is not suitable for real-time estimation of a road surface condition.

On the other hand, in the method for detecting the vibration level of a tire tread, when the road surface μ drops, for instance, the vibration level of high frequencies rises and conversely the vibration level of low frequencies lowers, so that there is only a small gain for the change in the OA power value of vibration in relation to the change in the road surface condition. As a result, the accuracy in estimating a road surface condition is not always sufficient.

The present invention has been made in view of these existing problems, and an object thereof is to provide not only a method and an apparatus for accurately estimating a road surface condition by improving the gain for the change in vibration level in relation to the change in road surface condition even when there are changes in temperature or vehicle speed, but also a road surface condition estimating tire that can be used in the estimation of a road surface condition.

Means for Solving the Problems

The inventors of the present invention have conducted earnest investigations and reached the realization that in the estimation of a road surface condition, three domains of tire vibration, i.e., a pre-leading domain, a contact patch domain, and a post-trailing domain, may be used. That is, vibration data from the pre-leading domain and the contact patch domain (pre-trailing domain), where temperature dependence is small, or vibration data from a frequency band with smaller temperature dependence, out of those from the pre-trailing domain and those from the post-trailing domain, are used. Also, a vibration level of a band of specific frequencies is extracted from the above-mentioned vibration data, and a road surface is estimated based on this extracted vibration level. In this manner, a road surface condition can be estimated with accuracy even when there are changes in temperature or vehicle speed. The present invention is based on this realization.

Thus, according to a first aspect of the present invention, there is provided a road surface condition estimating method comprising: detecting the vibration of a tire of a running vehicle; dividing the detected tire vibration into vibration in a pre-trailing domain, the domain existing before a trailing edge position, and vibration in a post-trailing domain, the domain existing after a trailing edge position, and at the same time extracting signals of tire vibration in the pre-trailing domain or signals of tire vibration in a time range corresponding to the pre-trailing domain; obtaining a frequency spectrum by analyzing the frequencies of the extracted signals; and thereafter calculating a vibration level in a predetermined frequency band from the obtained frequency spectrum; and estimating a road surface condition based on the calculated vibration level.

According to a second aspect of the present invention, there is provided a road surface condition estimating method comprising: detecting the vibration of a tire of a running vehicle; dividing the detected tire vibration into vibration in a pre-trailing domain, the domain existing before a trailing edge position, and vibration in a post-trailing domain, the domain existing after a trailing edge position, and at the same time extracting signals of tire vibration in the pre-trailing domain or signals of tire vibration in a time range corresponding to the pre-trailing domain; obtaining a time-series waveform of tire vibration including only the frequencies in a predetermined frequency range by passing the extracted signals through a band-pass filter of the predetermined frequency band; and thereafter calculating a vibration level in the predetermined frequency band from the obtained time-series waveform of tire vibration; and estimating a road surface condition based on the calculated vibration level.

According to a third aspect of the present invention, there is provided a road surface condition estimating method as recited in Claim 1 or 2, wherein the pre-trailing domain is any or all of a pre-leading domain, the domain existing before a leading edge position, a contact patch domain, the domain existing from the point of tire touching a road surface to the point of tire leaving it, and a domain covering the pre-leading domain and contact patch domain.

According to a fourth aspect of the present invention, there is provided a road surface condition estimating method as recited in any one of Claims 1 to 3, wherein the trailing edge position is estimated from a peak position of the tire vibration appearing near the tire contact patch.

According to a fifth aspect of the present invention, there is provided a road surface condition estimating method as recited in Claim 4, wherein the peak position of tire vibration is the peak position of tire vibration in the tire circumferential direction or the tire width direction occurring at a trailing edge.

According to a sixth aspect of the present invention, there is provided a road surface friction coefficient estimating method as recited in Claim 3, wherein a wheel speed is measured and a length of the pre-trailing domain of tire vibration or a time range corresponding to the pre-trailing domain is determined from data of the measured wheel speed.

According to a seventh aspect of the present invention, there is provided a road surface condition estimating method as recited in any one of Claims 1 to 6, wherein vibration levels in at least two frequency bands are calculated from the frequency spectrum or the time-series waveform, and a road surface condition is estimated from a vibration level computed value calculated using the plurality of calculated vibration levels.

According to an eighth aspect of the present invention, there is provided a road surface condition estimating method as recited in any one of Claims 1 to 7, wherein signals of tire vibration of a running vehicle of at least two predetermined positions in the pre-trailing domain or at least two predetermined time ranges before the trailing edge time are extracted, and a road surface condition is estimated using a vibration level computed value calculated using the vibration level values of the plurality of signals or the plurality of vibration levels.

According to a ninth aspect of the present invention, there is provided a road surface condition estimating method as recited in any one of Claims 1 to 8, wherein the lower-limit frequency in the predetermined frequency band or the lower-limit frequency of at least one of the two frequency bands is 2,000 Hz or above.

According to a tenth aspect of the present invention, there is provided a road surface condition estimating method as recited in Claim 1 or any one of Claims 3 to 6, wherein in addition to a vibration level of a predetermined frequency band obtained from a frequency spectrum of the pre-trailing domain, a vibration level in a frequency band lower than the predetermined frequency range is calculated from a frequency spectrum obtained by analyzing the frequencies of signals of the post-trailing domain, and a road surface condition is estimated based on a vibration level computed value calculated using the calculated vibration level in the pre-trailing domain and vibration level in the post-trailing domain.

According to a eleventh aspect of the present invention, there is provided a road surface condition estimating method as recited in any one of Claims 2 to 6, wherein in addition to a vibration level of a predetermined frequency band obtained from a time-series waveform of tire vibration in the pre-trailing domain obtained through a band-pass filter of the predetermined frequency band, a vibration level of a frequency band lower than the predetermined frequency band in the post-trailing domain, the frequency band obtained by passing signals of the post-trailing domain through a band-pass filter of the frequency band lower than the predetermined frequency range, is calculated, and a road surface condition is estimated based on a vibration level computed value calculated using the calculated vibration level in the pre-trailing domain and vibration level in the post-trailing domain.

According to a twelfth aspect of the present invention, there is provided a road surface condition estimating method as recited in Claim 10 or Claim 11, wherein the lower frequency band is selected from a frequency band of 0.5 to 4 kHz, and the higher frequency band is selected from a frequency band of 2 to 10 kHz.

According to a thirteenth aspect of the present invention, there is provided a road surface condition estimating method as recited in any one of Claims 10 to 12, wherein a wheel speed is measured and either or both of the lower frequency band and higher frequency band are changeable according to the data of the wheel speed.

According to a fourteenth aspect of the present invention, there is provided a road surface condition estimating method as recited in any one of Claims 10 to 12, wherein either or both of the lower frequency band and higher frequency band are changeable according to tire type.

According to a fifteenth aspect of the present invention, there is provided a road surface condition estimating method as recited in any one of Claims 10 to 14, wherein the vibration of a tire of a running vehicle is detected at least two points on the tire, vibration level computed values therefor are calculated respectively, and a road surface condition is estimated using an average value of the calculated vibration level computed values.

According to a sixteenth aspect of the present invention, there is provided a road surface condition estimating method as recited in anyone of Claims 1 to 15, wherein a relationship between various road surface conditions and the vibration level or the vibration level computed value is determined previously, and a road surface condition is estimated based on the relationship.

According to a seventeenth aspect of the present invention, there is provided a road surface condition estimating method as recited in any one of Claims 1 to 16, wherein a road surface is decided to be slippery when the vibration level or vibration level computed value exceeds a predetermined threshold value.

According to an eighteenth aspect of the present invention, there is provided a road surface condition estimating method as recited in any one of Claims 1 to 17, wherein a vibration level of one or a plurality of specific frequency bands in a specific range within the pre-leading domain of tire vibration is calculated, and a decision is made as to whether an intervening matter exists between road surface and tire based on a vibration level computed value calculated from the vibration level or the plurality of vibration levels.

According to a nineteenth aspect of the present invention, there is provided a road surface condition estimating method as recited in Claims 18, wherein an intervening matter is decided to exist between road surface and tire when the vibration level or vibration level computed value in the specific frequency band exceeds a predetermined threshold value.

According to a twentieth aspect of the present invention, there is provided a road surface condition estimating method as recited in Claim 18 or Claim 19, wherein frequencies in the specific frequency band are frequencies that increase or decrease in relation to the vehicle speed.

According to a twenty-first aspect of the present invention, there is provided a road surface condition estimating method as recited in Claim 20, wherein the specific frequency band is a frequency band including a pattern pitch frequency of tire vibration.

According to a twenty second aspect of the present invention, there is provided a road surface condition estimating method as recited in Claim 20, wherein the specific frequency band is a frequency band whose lower-limit frequency is higher than a pattern pitch frequency of tire vibration.

According to a twenty-third aspect of the present invention, there is provided a road surface condition estimating method as recited in Claim 17 or any one of Claims 19 to 22, wherein the threshold value is changed according to the data of wheel speed.

According to a twenty-fourth aspect of the present invention, there is provided a road surface condition estimating method as recited in Claim 17 or any one of Claims 19 to 22, wherein the threshold value is changed according to tire type.

According to a twenty-fifth aspect of the present invention, there is provided a road surface condition estimating method as recited in any one of Claims 1 to 24, wherein a road surface condition is estimated by detecting vibration at least two points on the tire circumference.

According to a twenty-sixth aspect of the present invention, there is provided a road surface condition estimating tire comprising: a tire vibration detecting means disposed on the air chamber side of an inner liner in a tire tread area, the tire vibration detecting means detecting the vibration of a tire of a running vehicle; and a signal extracting means for extracting signals of the pre-trailing domain of the tire vibration detected by the tire vibration detecting means.

According to a twenty-seventh aspect of the present invention, there is provided a road surface condition estimating tire as recited in Claim 26, further comprising: a frequency analysis means for analyzing the frequencies of signals extracted by the signal extracting means; and a vibration level calculating means for calculating a vibration level of a predetermined frequency band from a frequency spectrum obtained by the frequency analysis means.

According to a twenty-eighth aspect of the present invention, there is provided a road surface condition estimating tire as recited in Claim 26, further comprising: a band-pass filter for extracting signals of a predetermined frequency band from signals extracted by the signal extracting means; and a vibration level calculating means for calculating a vibration level of the predetermined frequency band from a time-series waveform of the extracted tire vibration.

According to a twenty-ninth aspect of the present invention, there is provided a road surface condition estimating tire as recited in Claim 27 or Claim 28, further comprising: a means for calculating vibration levels of at least two frequency bands from the frequency spectrum or the time-series waveform; and a means for calculating a vibration level computed value using the plurality of calculated vibration levels.

According to a thirtieth aspect of the present invention, there is provided a road surface condition estimating tire as recited in Claim 26, further comprising: a signal extracting means for extracting signals tire vibration in the post-trailing domain, in addition to the signals of tire vibration in the pre-trailing domain.

According to a thirty-first aspect of the present invention, there is provided a road surface condition estimating tire as recited in Claim 30, further comprising: a frequency analysis means for analyzing the frequencies of the signals of the pre-trailing domain and signals of the post-trailing domain extracted by the signal extracting means; a vibration level calculating means for calculating a vibration level of a frequency band, the lower-limit frequency of which being 0.5 kHz or above and the upper-limit frequency of which being 4 kHz or below, from a frequency spectrum of the post-trailing domain obtained by the frequency analysis means, and a vibration level of a frequency band, the lower-limit frequency of which being 2 kHz or above and the upper-limit frequency of which being 10 kHz or below, from a frequency spectrum of the pre-trailing domain obtained thereby; and a means for calculating a vibration level computed value using the calculated vibration level in the post-trailing domain and vibration level in the pre-trailing domain.

According to a thirty-second aspect of the present invention, there is provided a road surface condition estimating tire as recited in Claim 30, further comprising: a band-pass filter for extracting respective signals of mutually different predetermined frequency bands by inputting the signals of the post-trailing domain and signals of the pre-trailing domain extracted by the signal extracting means; a vibration level calculating means for calculating a vibration level of a frequency band, the lower-limit frequency of which being 0.5 kHz or above and the upper-limit frequency of which being 4 kHz or below, from the extracted time-series waveform of the post-trailing domain, and a vibration level of a frequency band, the lower-limit frequency of which being 2 kHz or above and the upper-limit frequency of which being 10 kHz or below, from the time-series waveform of the pre-trailing domain; and a means for calculating a vibration level computed value using the calculated vibration level in the post-trailing domain and vibration level in the pre-trailing domain.

According to a thirty-third aspect of the present invention, there is provided a road surface condition estimating tire as recited in any one of Claims 26 to 32, further comprising: a means for wirelessly transmitting data of the vibration level or vibration level computed value to the vehicle body side.

According to a thirty-fourth aspect of the present invention, there is provided a road surface condition estimating tire as recited in any one of Claims 26 to 33, wherein the tire vibration detecting means is a tire vibration detecting means for detecting tire vibration in the circumferential direction.

According to a thirty-fifth aspect of the present invention, there is provided a road surface condition estimating tire as recited in any one of Claims 26 to 33, wherein the tire vibration detecting means is a tire vibration detecting means for detecting vibration in the tire width direction.

According to a thirty-sixth aspect of the present invention, there is provided a road surface condition estimating tire as recited in (any one of) Claims 26 to 35, wherein the tire vibration detecting means is disposed at the center of the tire width.

According to a thirty-seven aspect of the present invention, there is provided a road surface condition estimating tire as recited in (any one of) Claims 26 to 35, wherein the tire vibration detecting means is disposed a predetermined distance apart in the width direction from the center of the tire width.

According to a thirty-eighth aspect of the present invention, there is provided a road surface condition estimating tire as recited in any one of Claims 26 to 37, wherein the tire vibration detecting means is a tire vibration detecting means capable of detecting up to 20,000 Hz of tire vibration.

According to a thirty-ninth aspect of the present invention, there is provided a road surface condition estimating tire as recited in any one of Claims 26 to 38, wherein the tire vibration detecting means is disposed at least two points on the tire circumference.

According to a fortieth aspect of the present invention, there is provided a road surface condition estimating apparatus as recited in Claim 40 comprising: a reception means for receiving data of a vibration level or a vibration level computed value wirelessly transmitted from a road surface condition estimating tire as recited in any one of Claims 33 to 39; and a road surface condition estimating means for estimating a road surface condition based on the received data of a vibration level or a vibration level computed value.

According to a forty-first aspect of the present invention, there is provided a road surface condition estimating apparatus as recited in Claim 40, further comprising: a storage means for storing a map of a previously determined relationship between various road surface conditions and the vibration level or the vibration level computed value, wherein a road surface condition is estimated using the received data of vibration level or vibration level computed value and the map.

According to a forty-second aspect of the present invention, there is provided a road surface condition estimating apparatus as recited in Claim 40, further comprising: a storage means provided on the tire side, the storage means storing a map of a previously determined relationship between various road surface conditions and the vibration level or the vibration level computed value; and a reading means provided on the vehicle body side, the reading means reading information of the map, wherein a road surface condition is estimated, on the vehicle body side, based on the map information read as above.

According to a forty-third aspect of the present invention, there is provided a road surface condition estimating apparatus as recited in any one of Claims 40 to 42, further comprising: a transmission means for wirelessly transmitting information of the estimated road surface condition to another vehicle.

According to a forty-fourth aspect of the present invention, there is provided a road surface condition estimating apparatus as recited in Claim 43, further comprising: a reception means for receiving the wirelessly transmitted information on a road surface condition; and a means for grasping a road surface condition ahead from information on a road surface condition transmitted from a vehicle running ahead.

According to a forty-fifth aspect of the present invention, there is provided a vehicle control apparatus as recited in Claim 45 comprising: a road surface condition estimating apparatus as recited in Claim 43; an inter-vehicular distance estimating means for estimating the distance to a vehicle ahead; a wheel speed detecting means; and a running condition control means for controlling the running condition of a vehicle based on road surface information from the means for grasping a road surface condition ahead, inter-vehicular distance information from the inter-vehicular distance estimating means, and wheel speed information from the wheel speed detecting means.

Effect of the Invention

According to the present invention, the vibration of a tire of a running vehicle is detected, and signals of the tire vibration in a predetermined domain before a trailing edge position (pre-trailing domain), such as the pre-leading domain, the contact patch domain, or the domain covering the pre-leading domain and the contact patch domain, or signals from a frequency band with relatively small temperature dependence, out of signals of the pre-training domain and signals of post-trailing domain, are extracted. Then a vibration level of a predetermined frequency band is calculated from a frequency spectrum obtained by analyzing the frequencies of the above-mentioned signals or from a time-series waveform of tire vibration obtained by passing the signals through a band-pass filter of a predetermined frequency band, and a road surface condition is estimated based on the calculated vibration level. Therefore, even when there are changes in temperature or vehicle speed, a road surface condition can be estimated with accuracy.

Also, signals of tire vibration of a running vehicle from at least two predetermined positions before the trailing edge position or signals from at least two predetermined time ranges before the trailing edge point (time) may be extracted and the plurality of signals may be used in estimating a road surface condition. Then a road surface condition can be estimated with even better accuracy.

In doing so, the trailing edge position may be estimated from a peak position of tire vibration in the circumferential direction appearing near the contact patch of tire, that is, from a peak position of tire vibration occurring at the leading edge point or a peak position of tire vibration in the circumferential direction occurring at the trailing edge point. Then the signals from the respective domains can be extracted reliably.

Also, vibration levels of at least two frequency bands may be calculated from the above-mentioned frequency spectrum or time-series waveform, and at the same time a frequency level computed value may be obtained using the calculated plurality of vibration levels. And this frequency level computed value may be used in estimating a road surface condition. Then a road surface condition can be estimated with even better accuracy.

Also, a vibration level or levels in one or a plurality of predetermined frequency bands in the pre-leading domain of tire vibration, which is a frequency band including a pattern pitch frequency or a frequency band whose lower-limit frequency is higher than the pattern pitch frequency and which increases or decreases with the vehicle speed, may be calculated, and a decision may be made as to the presence or absence of an intervening matter between road surface and tire, based on a vibration level computed value calculated from the above-mentioned vibration level or levels. Then it is possible to easily and reliably estimate whether or not there is an intervening matter, such as water or snow, on the road surface.

Also, in addition to the above-mentioned vibration level in the pre-trailing domain, a vibration level of a frequency band selected from a 0.5 to 4 kHz range in the post-trailing domain may be calculated from a frequency spectrum obtained by detecting a time-series waveform of tire vibration in the post-trailing domain and analyzing the frequencies thereof. And a vibration level computed value may be calculated using this calculated vibration level and the vibration level of a frequency band selected from a 2 to 10 kHz range of the above-mentioned tire vibration in the pre-trailing domain, which is calculated from a frequency spectrum obtained by detecting a time-series waveform thereof and analyzing the frequencies thereof. Then a road surface condition can be estimated with accuracy based on the vibration level computed value thus calculated.

Also, a vibration level in the pre-trailing domain and a vibration level in the post trailing domain may be calculated respectively from their respective time-series waveforms obtained by passing the time-series waveform of tire vibration through a band-pass filter of a predetermined frequency band, and a vibration level computed value may be obtained. This can also produce a similar effect.

Also, it may be so arranged that a road surface is decided to be slippery when a vibration level or a vibration level computed value exceeds a predetermined threshold value. Such an arrangement can allow easy acquisition of information that can be used to improve the running safety of a vehicle.

Also, the running condition of a vehicle may be controlled using information on a road surface condition estimated as described above. Such an arrangement can improve the running safety of a vehicle markedly.

BEST MODE FOR CARRYING OUT THE INVENTION

The best mode for carrying out the present invention will be described hereinbelow by reference to the accompanying drawings.

Embodiment 1

Figure 1:
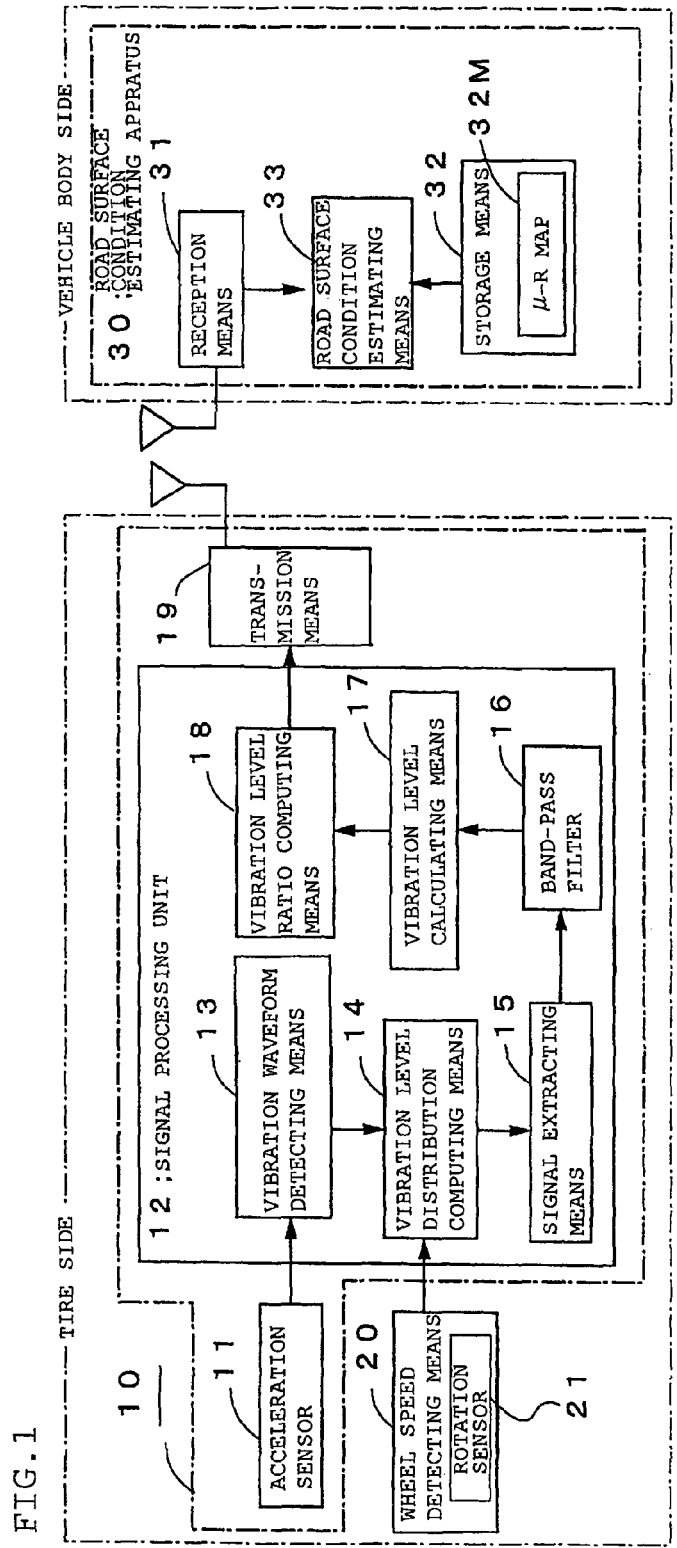
FIG. 1 is a function block diagram showing a structure of a road surface condition estimating system according to Embodiment 1 of the present invention.

FIG. 1 is a function block diagram showing a structure of a road surface condition estimating system according to Embodiment 1 of the present invention. In FIG. 1, 10 is a road surface condition estimating tire which is provided with an acceleration sensor 11 as a vibration detecting means for detecting vibration inputted to the tire and a signal processing unit 12 for calculating a vibration level or a vibration level computed value of tire vibration by processing the signal output of the acceleration sensor 11 and transmitting it to the vehicle body side. 20 is a wheel speed detecting means, equipped with a rotation sensor 21, for detecting the rotation speed of the wheel. And 30 is a road surface condition estimating apparatus, provided on the vehicle body side, for estimating the condition of a road surface on which the vehicle is running from the vibration level or the vibration level computed value transmitted from the road surface condition estimating tire 10.

Figure 2:
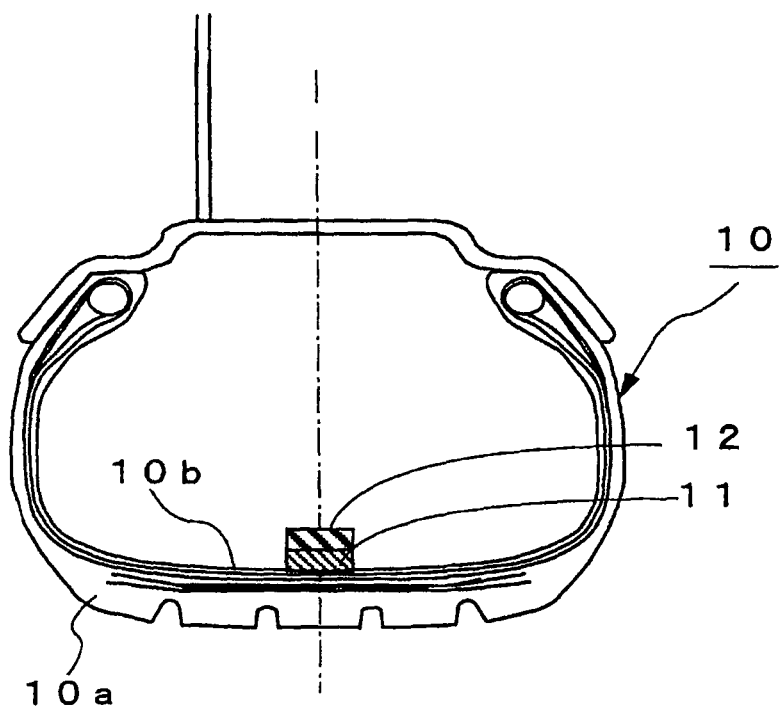
FIG. 2 shows an example of fitting position of an acceleration sensor.

In the present embodiment, a sensor capable of detecting up to 20,000 Hz of vibration acceleration is used as the acceleration sensor 11. Also, as shown in FIG. 2, the acceleration sensor 11 and the signal processing unit 12 are disposed nearly at the center of an inner liner portion 10b of a tire tread 10a on the tire air chamber side in order to detect the vibration inputted to the tire. Also, in the present embodiment, the acceleration sensor 11, which is so arranged to detect in the tire circumferential direction, detects tire vibration in the circumferential direction.

Figure 3:
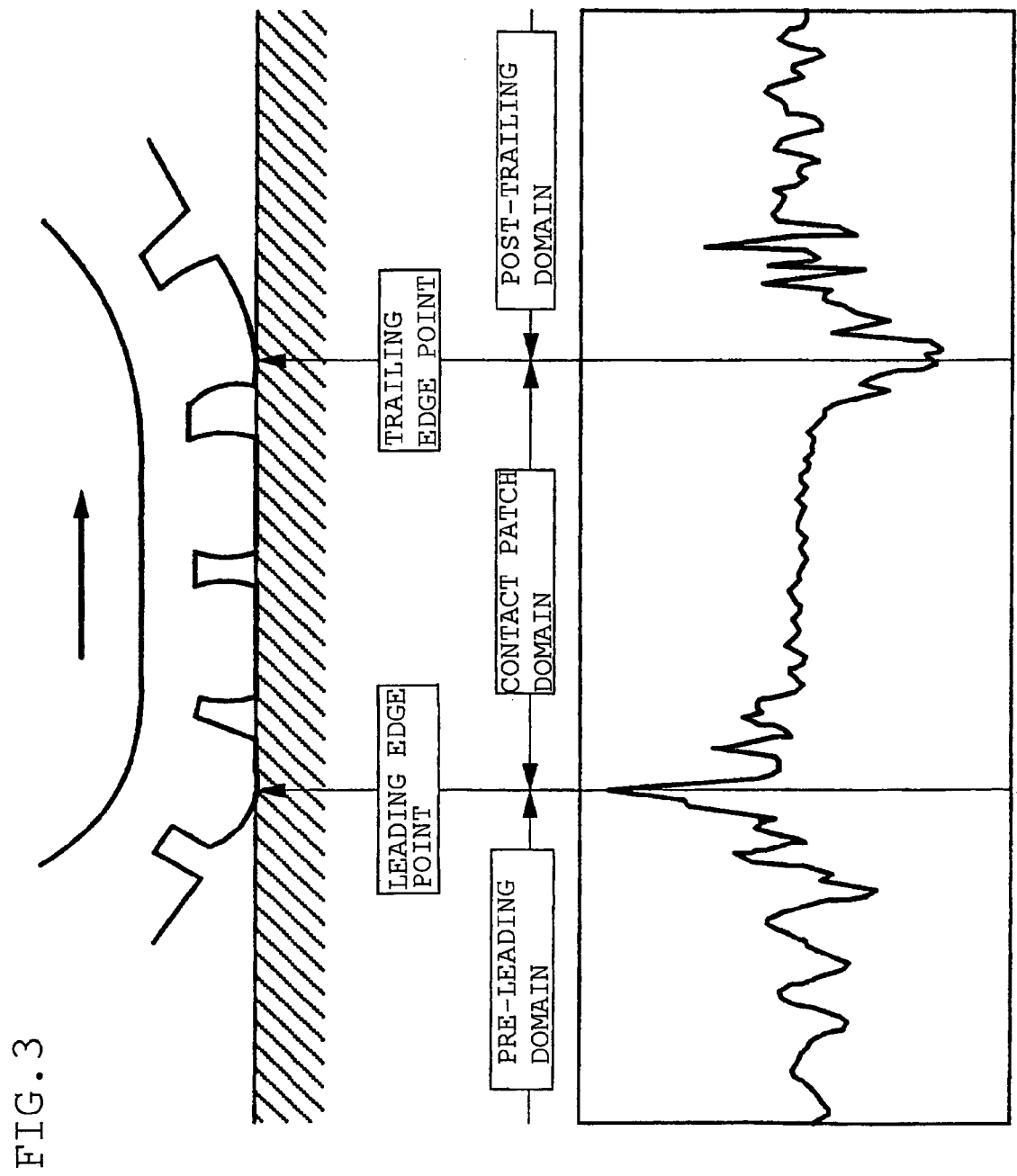
FIG. 3 is an illustration showing the pre-leading domain, the contact patch domain, and the post-trailing domain of a tire vibration waveform.

The signal processing unit 12 installed on the road surface condition estimating tire 10 is provided, specifically, with a vibration waveform detecting means 13 for obtaining a vibration waveform by arranging the output levels (vibration levels) of the acceleration sensor 11 in a time series; a vibration level distribution computing means 14 for obtaining a distribution of vibration levels inputted to a tire tread 10a by converting the vibration waveform into vibration waveforms corresponding to predetermined positions on a tire by using output pulses from the rotation sensor 21; a signal extracting means 15 for identifying an accurate trailing edge position of the tire 10 from a peak position of tire vibration that appears in the vicinity of a tire contact patch, at the same time dividing data of the vibration level distribution into data in three regions, namely, the pre-leading domain, the contact patch domain, and the post-trailing domain, as shown in FIG. 3, and extracting the respective data of vibration levels in the pre-leading domain and the contact patch domain (hereinafter these two domains or the domain covering these two domains being referred to as "pre-trailing domain") out of the above-mentioned domains; a band-pass filter 16 for extracting a vibration component of a low frequency band (e.g., 1 to 2 kHz band) and a vibration component of a high frequency band (e.g., 3 to 5 kHz band) from the respective extracted data of vibration levels; a vibration level calculating means 17 for calculating a power value of the low-frequency vibration level and a power value of the high-frequency vibration level in the pre-trailing domain having passed through the band-pass filter 16; a vibration level ratio computing means 18 for calculating a vibration level ratio R, which is a ratio of the power value of high-frequency vibration level to the power value of low-frequency vibration level in the pre-trailing domain calculated as above; and a transmission means 19. And the signal processing unit 12 transmits data of a vibration level computed value (a vibration level ratio R here) obtained by processing the output signals of the acceleration sensor 11.

Also, the road surface condition estimating apparatus 30, which is provided with a reception means 31 for receiving data of a vibration level computed value transmitted from the tire 10, a storage means 32 for storing a map 32M showing a previously obtained relationship between road surface conditions and the vibration level ratio R of tire vibration, and a road surface condition estimating means 33 for estimating the condition of a road surface on which the vehicle is running, based on the received data of a vibration level ratio R and the map 32M, estimates a road surface condition based on the vibration level computed value transmitted from the road surface condition estimating tire 10.

Figure 4:
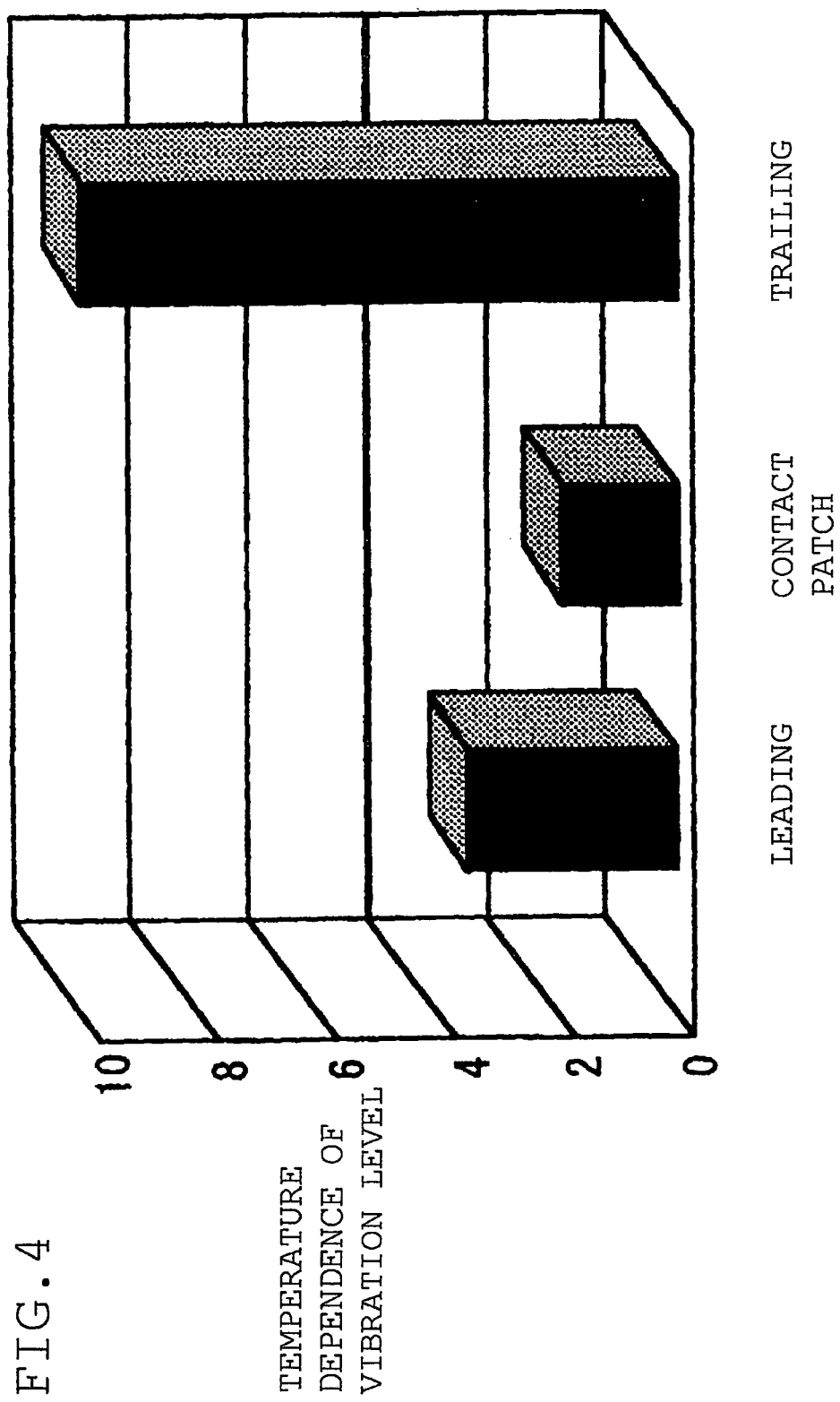
FIG. 4 is a graph showing a comparison of the temperature dependence of vibration level in a 4 to 5 kHz band between the pre-leading domain, the contact patch domain and the post-trailing domain.

It should be noted that the vibration levels as mentioned above have temperature dependence. FIG. 4 shows a comparison of temperature dependence of the respective vibration levels in a 4 to 5 kHz band in the pre-leading domain, the contact patch domain, and the post-trailing domain. Here, the vertical axis represents the standardized value of the degree of temperature dependence of vibration level, which is the ratio of vibration level at 0° C. to vibration level at 30° C., 10 representing the value in the post-trailing domain where the degree of temperature dependence is the greatest. It is evident that the degree of temperature dependence of vibration level differs from each other in the pre-leading domain, the contact patch domain, and the post-trailing domain and that the temperature dependence in the trailing domain is far greater than those in the pre-leading domain and the contact patch domain. Therefore, in this embodiment, only the vibration levels in the pre-leading domain and the contact patch domain are used as the vibration levels for the estimation of a road surface condition in order to improve the system's robustness against temperature disturbance.

Note, however, that since the vibration level of a relatively low frequency band (0.5 kHz to 4 kHz), out of the vibration levels in the post-trailing domain, has a low degree of temperature dependence, a vibration level of a relatively low frequency band in the post-trailing domain, in addition to the vibration levels in the pre-trailing domain, may also be used as the vibration level for the estimation of a road surface condition.

Next, a description will be given of a method for estimating a road surface condition according to Embodiment 1.

Firstly, an acceleration sensor 11 detects the circumferential-direction vibration of a tire of a running vehicle and sends the output to a vibration waveform detecting means 13, where a vibration waveform in the tire circumferential direction arranged in a time series is obtained. Then a vibration level distribution computing means 14 processes the vibration waveform and thereby establishes correspondence of a leading edge position and a trailing edge position to the time axis of the vibration waveform arranged in a time series.

In the present embodiment, a signal extracting means 15 identifies an actual trailing edge position on the tire 10 from the vibration waveform and then a leading edge position thereon based on the thus identified trailing edge position, and at the same time divides the data of vibration level distribution into the data in three domains, namely, the pre-leading domain, the contact patch domain, and the post-trailing domain as shown in FIG. 3.

Figure 5:
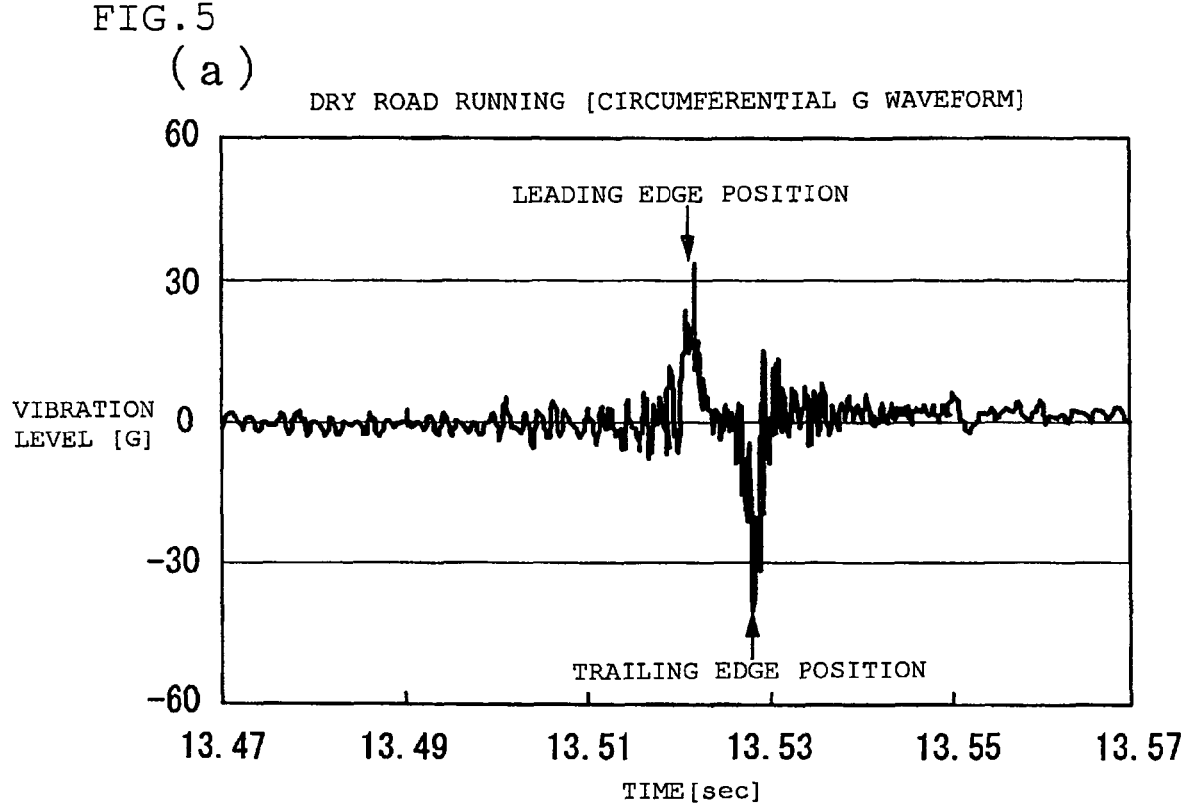
FIG. 5 shows a vibration waveform when a vehicle fitted with a road surface condition estimating tire is driven at a constant speed on a dry asphalt road and an ice-covered road, respectively.
Figure 5:
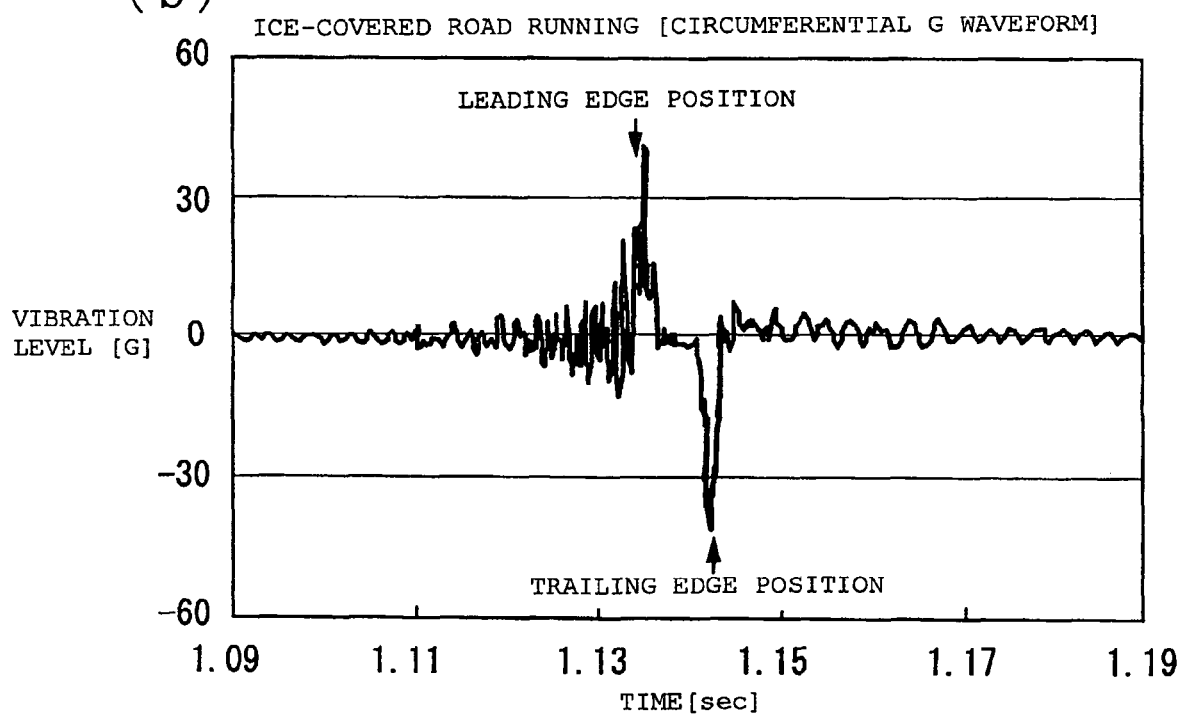

FIG. 5A shows a vibration waveform arranged in a time series, with the leading edge position and the trailing edge position corresponding thereto, when a vehicle fitted with a road surface condition estimating tire 10 according to the present invention is driven at a constant speed on a dry asphalt road surface ($\mu \approx 1$). FIG. 5B shows a vibration waveform, with the tire tread position corresponding thereto, when the vehicle is driven on an ice-covered road surface ($\mu \approx 0.1$). As is clear from the above-mentioned vibration waveforms, the peak of tire vibration is conspicuous at the trailing edge position whether on a dry asphalt road or on an ice-covered road, and the peak position may be easily identified irrespective of the road surface condition. Therefore, identification of the trailing edge position from a vibration waveform may determine the above-mentioned three domains with better accuracy than where the leading edge position and the trailing edge position are identified from data of the output pulses from a rotation sensor 21.

Note that an actual leading edge position of a tire 10 may be identified from a vibration waveform instead of from the above-mentioned trailing edge position, and the trailing edge position may be identified on the basis of the thus identified leading edge position. However, on a snow-covered road surface, a wet road surface, or the like, the peak of vibration comes in the pre-leading domain as will be described later, and hence it is preferable that, as in this embodiment, the trailing edge position be identified first and then the leading edge position from the trailing edge position.

A signal extracting means 15 extracts the respective data of vibration levels in the pre-leading domain and the contact patch domain out of the above-mentioned domains and then has the extracted data of vibration levels in the respective domains pass through a band-pass filter 16, thereby extracting a vibration component of a low frequency band (e.g., 1 to 2 kHz band) and a vibration component of a high frequency band (e.g., 3 to 5 kHz band), respectively, in the pre-leading domain and the contact patch domain.

A vibration level calculating means 17 calculates a power value of the low-frequency vibration level and a power value of the high-frequency vibration level in each of the above-mentioned domains, and a vibration level ratio computing means 18 calculates the respective vibration level ratios R, which are each a ratio of the power value of high-frequency vibration level to the power value of low-frequency vibration level in each of the domains calculated as above. And a transmission means 19 transmits the data of the vibration level ratios R calculated as above to a road surface condition estimating apparatus 30.

At the road surface condition estimating apparatus 30, a reception means 31 receives the data of the vibration level ratios, and a road surface condition estimating means 33 estimates the condition of a road surface on which the vehicle is running, based on the vibration level ratios R and a map 32M stored in a storage means 32, which shows a relationship between the vibration level ratio R and road surface conditions.

Generally, when the road surface friction coefficient μ is high, the tire in the contact patch domain develops little vibration because it is gripped by the road surface. As the road surface μ lowers, however, the grip between the tire and the road surface declines, so that tire vibration due to slippage occurs in both the pre-leading domain and contact patch domain. Also, the low-frequency component of tire vibration as described above is caused by a flattened deformation of a tire on the road surface or a collision of the tire and the road surface and is dependent on the surface roughness of a road and the speed of the vehicle. And the high-frequency component thereof is caused by slips between tire and road surface. Accordingly, the vibration level ratio R varies with the road surface condition, or the value of the road surface friction coefficient μ.

In the present invention, as stated already, the vibration level ratio R is calculated using a low-frequency band of 1 to 2 kHz and a high-frequency band of 3 to 5 kHz. The vibration level ratio R is small on a dry asphalt road surface (μ≈1), which is a high μ road surface, and it is large on an ice-covered road surface (μ≈0.1), which is a low μ road surface. Therefore, by preparing a map 32M showing a previously determined relationship between the vibration level ratio R and road surface conditions (e.g., high μ road, medium μ road, low μ road) when a vehicle runs on various types of road surface and storing it in a storage means 32, it is possible to accurately estimate the condition of a road surface on which a vehicle is running, by comparing the map 32M and the vibration level ratio R computed as described above.

It should be noted that if a map showing a relationship between the vibration level ratio R and the road surface friction coefficient μ, instead of the map 32M, is prepared, the road surface friction coefficient μ may also be estimated with accuracy.

Also, in the present embodiment, the vibration levels in only the pre-leading domain and the contact patch domain, where they are less affected by the influence of temperature, are used as the vibration levels for the estimation of a road surface condition. And this can improve the robustness of the system against temperature disturbance.

Thus, according to the present Embodiment 1, a road surface condition estimating tire 10, provided with an acceleration sensor 11 for detecting vibration inputted to the tire and a signal processing unit 12 for processing the output signals of the acceleration sensor 11 and transmitting the result to the vehicle body side, detects the vibration of the tire of a running vehicle in the circumferential direction and identifies an exact trailing edge position of the tire 10 from the vibration waveform. At the same time, the data of the vibration waveform are divided into data for three domains, namely, the pre-leading domain, the contact patch domain, and the post-trailing domain, and the respective data of vibration levels in the pre-leading domain and the contact patch domain out of the above-mentioned domains are extracted. Then a vibration component of a low-frequency band and a vibration component of a high frequency band in the pre-leading domain and the contact patch domain, respectively, are extracted from the extracted data of vibration levels in the respective domains. And the respective vibration level ratios R, which are each a ratio between the power values thereof, are calculated, and the results are transmitted to a road surface condition estimating apparatus 30 on the vehicle body side. Then, on the vehicle body side, the condition of a road surface on which the vehicle is running is estimated, based on the received data of the vibration level ratios R and a map 32M stored in a storage means 32, which shows a relationship between the vibration level ratio R and road surface conditions. Thus, even when there are changes in temperature or vehicle speed, a road surface condition can be estimated with accuracy.

In Embodiment 1 as described above, tire vibration in the circumferential direction detected at the width center of a tire tread 21 is detected by an acceleration sensor 11. However, the vibration detecting direction of the acceleration sensor 11 may be the width direction of a tire; that is, the vibration at a tread edge, which develops a deformation opposite to the one near the tread center, may be detected, so that the vibration in the tire width direction may be detected.

Also, the above-mentioned acceleration sensor 11 may be disposed at the center of tire width. However, if tire deformation due to slippage on a low μ L road is to be taken into consideration, disposing it a predetermined distance from the tire width center in the width direction is more advantageous because the vibration level ratio R then is larger.

Also, on an ice-covered road surface, where variation in vibration level data is wide, it is preferable that a plurality of acceleration sensors 11 be arranged on the tire circumference and an average value of vibration levels or vibration level computed values obtained by the plurality of the sensors be used for the estimation of a road surface condition. This way, the estimation accuracy of a road surface condition may be further improved.

Also, in the above-mentioned embodiment, the low-frequency band selected is 1 to 2 kHz, and the high-frequency band selected is 3 to 5 kHz, but the arrangement is not limited thereto. Those frequency bands may be set as appropriate, according to tire type, vehicle speed, or the like. In such a case, too, it is preferable that the high-frequency band be a frequency band whose lower-limit value is 2,000 Hz or above so that there may be marked differences in vibration level ratio between road surface conditions.

Also, in the above-described embodiment, a vibration component of a low frequency band and a vibration component of a high frequency band are extracted by a band-pass filter 16, and then a power value of the low-frequency vibration level and a power value of the high-frequency vibration level in each of the above-mentioned domains are calculated. However, instead of the band-pass filter 16, a frequency analysis means capable of analyzing the frequencies of data of respective vibration levels to obtain their frequency spectrums may be provided, and a power value for the vibration level of the low-frequency band and a power value for the vibration level of the high-frequency band may be calculated from the thus obtained frequency spectrums in the respective domains.

Also, in the above-described embodiment, a road surface condition is estimated using a map 32M which shows a previously determined relationship between the vibration level ratio R of tire vibration and road surface conditions. However, instead of using the map 32M, a threshold value K may be set for the vibration level ratio R, and a decision may be made such that the road surface is a high μ road surface when the vibration level ratio R is at or below the threshold value K and it is a low μ road surface when the vibration level ratio R is above the threshold value K. Or threshold values K1 and K2 may be set, and a decision may be made such that the road surface is a high μ road surface when R≤K1, a medium μ road surface when K1<R≤K2, or a low μ road surface when K2<R.

It is to be noted that the map 32 showing a relationship between the vibration level ratio R of tire vibration and road surface condition varies with tire type. Hence, if many tire types are involved, the storage means 32 is required to have a large capacity. In such a case, a storage means for storing a map for an applicable tire type may be installed on a road surface condition estimating tire 10, and at the same time a means for reading information on the map may be provided on the tire side. In this case, the storage means 32 only has to store the map for the applicable tire type which is read as mentioned above. As a result, the capacity of the storage means 32 can not only be small, but also the operation to retrieve the map may be eliminated. In this manner, the computation speed may be raised.

Embodiment 2

In Embodiment 1 heretofore described, a road surface condition is estimated from the vibration level ratio R. On a wet road, snow-covered road or the like, where there is an intervening matter, such as water or snow, lying on the road surface, however, the tire hits a water film before it hits the road surface, so that the vibration level rises before the presumed peak position in the leading edge portion. Since the main frequency of this vibration changes with the tread pattern pitch of an applicable tire, it is possible to use the vibration level of a band which includes the pattern pitch frequency as an indicator of whether there is an intervening matter, such as mentioned above, on the road surface.

Therefore, a road surface condition may be estimated by calculating the pattern pitch frequency from the data of tread pattern of an applicable tire and the data of wheel speed and using the vibration level of a band including the pattern pitch frequency as an indicator of whether there is an intervening matter on the road surface.

Figure 6:
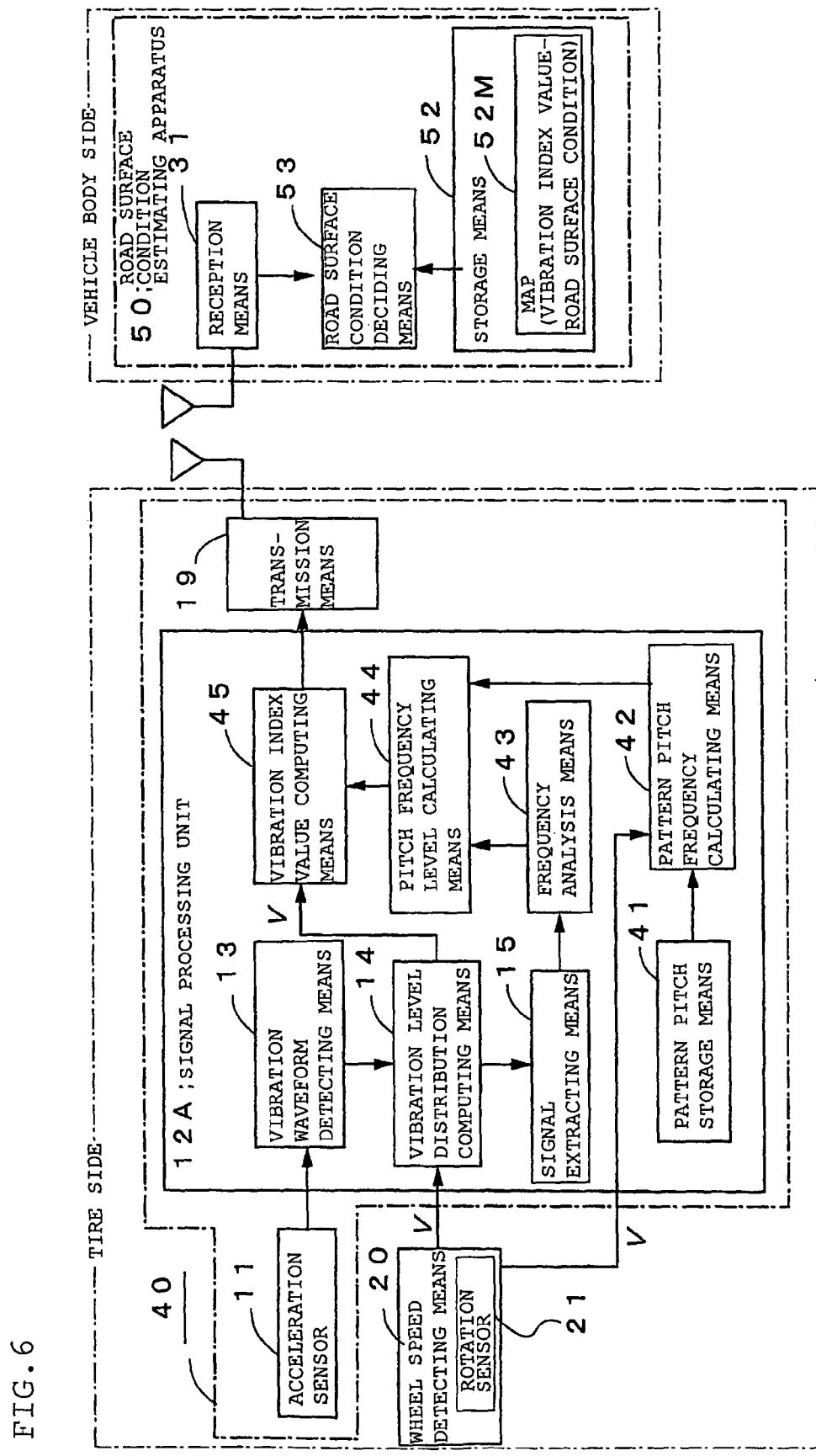
FIG. 6 is a function block diagram showing a structure of a road surface condition estimating system according to Embodiment 2.

FIG. 6 is a block diagram showing a structure of a road surface condition estimating system according to Embodiment 2 (best mode 2) of the present invention. A road surface condition estimating tire 40 comprises an acceleration sensor 11, a signal processing unit 12A, and a transmission means 19, of which the signal processing unit 12A further comprises a pattern pitch storage means 41 for storing a pattern pitch of an applicable tire and a pattern pitch frequency calculating means 42 for calculating a pattern pitch frequency at the current vehicle speed from the data of the pattern pitch and data of wheel speed detected by a wheel speed detecting means 20, as additions to the identical components of the signal processing unit 12 of Embodiment 1, a frequency analysis means 43 for analyzing the frequencies of data of vibration level in the pre-leading domain and the contact patch domain extracted by the signal extracting means 15 and thereby obtaining the frequency spectrum thereof, a pitch frequency level calculating means 44 for extracting a vibration level of a predetermined frequency range including the pattern pitch frequency from the obtained frequency spectrum and calculating a power value of the vibration level, and a vibration index computing means 45 for computing a pitch vibration index, which is a ratio between the calculated power value of vibration level of the pitch frequency band and the wheel speed detected by the wheel speed detecting means 20, the preceding three means 43, 44, and 45 replacing the band-pass filter 16, the vibration level calculating means 17 and the vibration level ratio computing means 18 of Embodiment 1. And the road surface condition estimating tire 40 transmits the computed value of pitch vibration index and data of vehicle speed to the vehicle body side from the transmission means 19 thereof.

On the other hand, a road surface condition estimating apparatus 50, which comprises a reception means 31, a storage means 52 for storing a map 52M showing a previously determined relationship between the pitch vibration index value for different vehicle speeds and road surface conditions, and a road surface condition deciding means 53 for deciding whether there is an intervening matter, such as water or snow, on the road surface where the vehicle is running from the received pitch vibration index value and vehicle speed by using the map 52M, decides whether there is an intervening matter, such as water or snow, on the road surface.

Note that the arrangement may also be such that a band-pass filter for extracting a vibration level of a band including the calculated pattern pitch frequency and a means for calculating a power value to calculate the vibration level of signals having passed through the band-pass filter are provided instead of the frequency analysis means 43 and the pitch frequency level calculating means 44.

EXAMPLE 1

Figure 7:
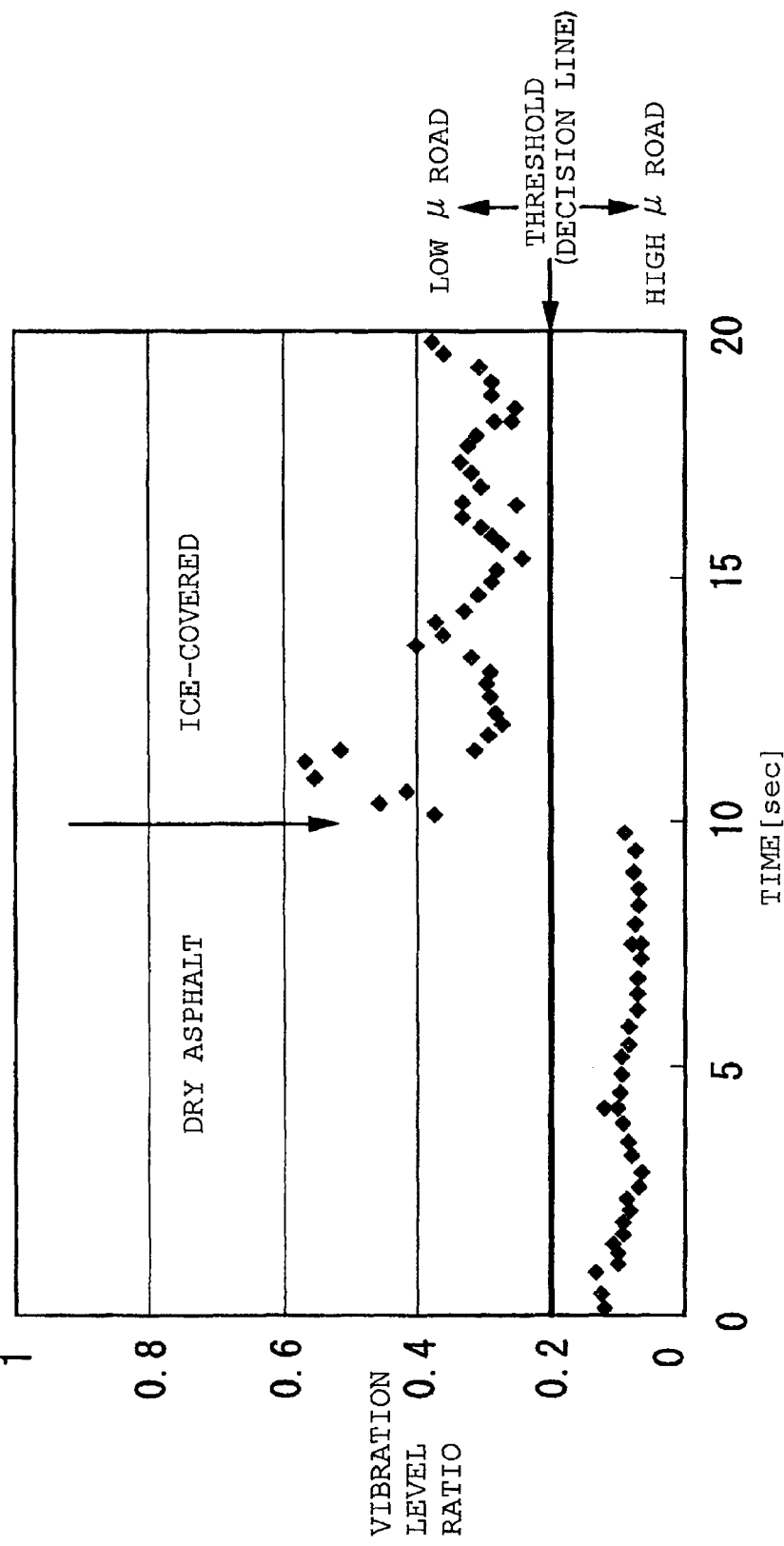
FIG. 7 is a diagram showing changes of vibration level ratio with time when a vehicle fitted with a road surface condition estimating tire is driven at a constant speed from a dry asphalt road onto an ice-covered road.

A vehicle fitted with a road surface condition estimating tire according to the present invention was driven at a constant speed from a dry asphalt road surface ($\mu \approx 1$) onto an ice-covered road surface ($\mu \approx 0.1$), and the change of the vibration level ratio with time was measured. The results are shown in FIG. 7. The horizontal axis of the figure represents time, and the vertical axis the standardized value (vibration level ratio R) of the power value of vibration level of a high-frequency band standardized by the power value of low-frequency vibration level in the pre-leading domain and the contact patch domain or the domain covering the pre-leading domain and the contact patch domain. It is evident that the vibration level ratio R increases simultaneously as the vehicle enters on the ice-covered road. This resulted from the detection of an increase in slippage due to lowered $\mu$ in the contact patch domain, and thus it has been confirmed that the slipperiness of a road surface can be decided by setting a proper threshold value.

EXAMPLE 2

Figure 8:
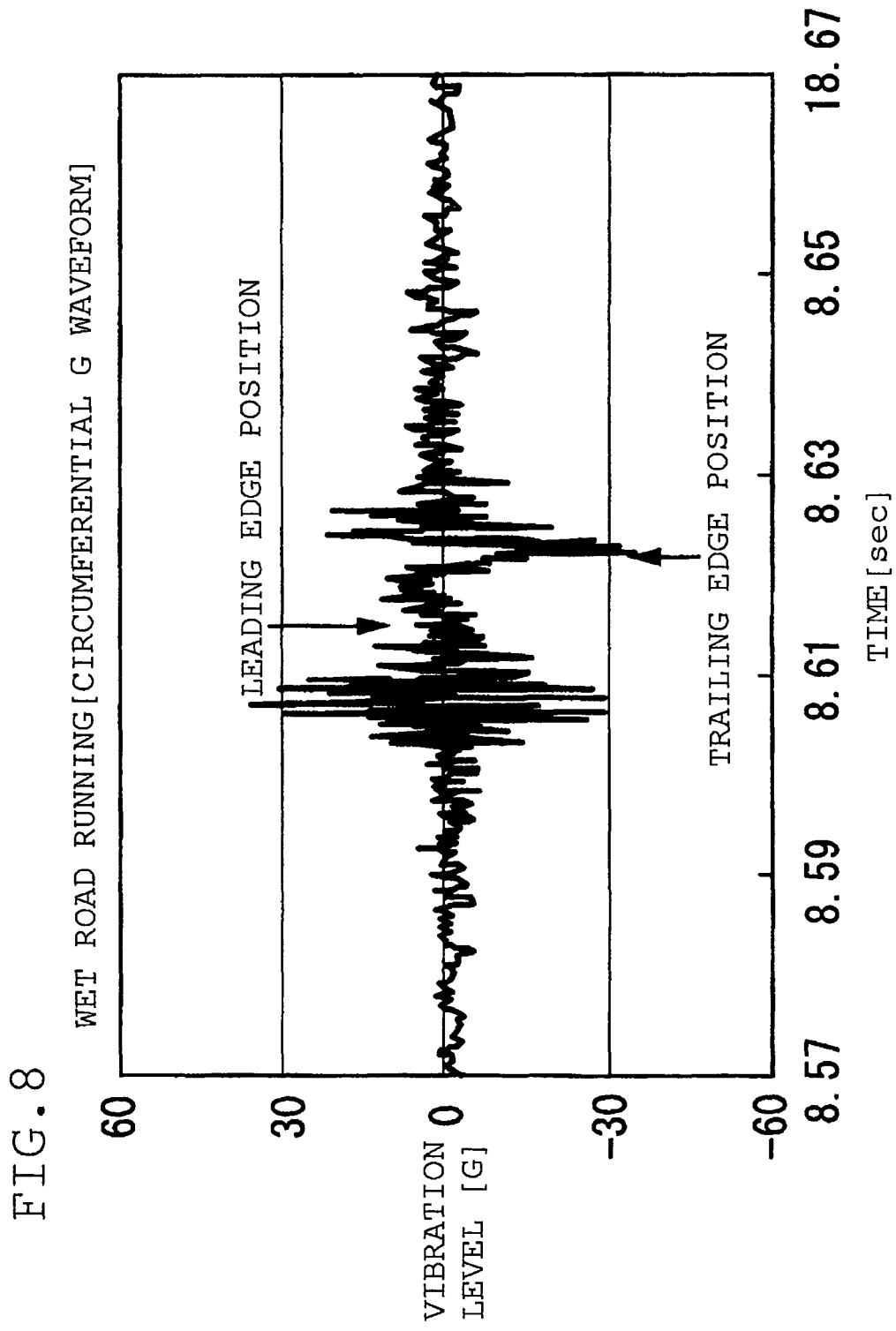
FIG. 8 is a diagram showing a waveform of tire circumferential-direction vibration when a vehicle fitted with a road surface condition estimating tire is driven a on a wet straight road.

A vehicle fitted with a road surface condition estimating tire according to the present invention was driven at 70 km/hr on a wet straight road (water depth: 10 mm), and the measured waveform of tire vibration in the circumferential direction is shown in FIG. 8. On a wet road, the tire strikes against a water film rather than the road surface, so that the vibration level is expected to rise before the presumed peak position in the leading edge portion as viewed from the contact patch length. In actuality, too, the vibration waveform shows that the vibration level rises before the leading edge point.

Figure 9:
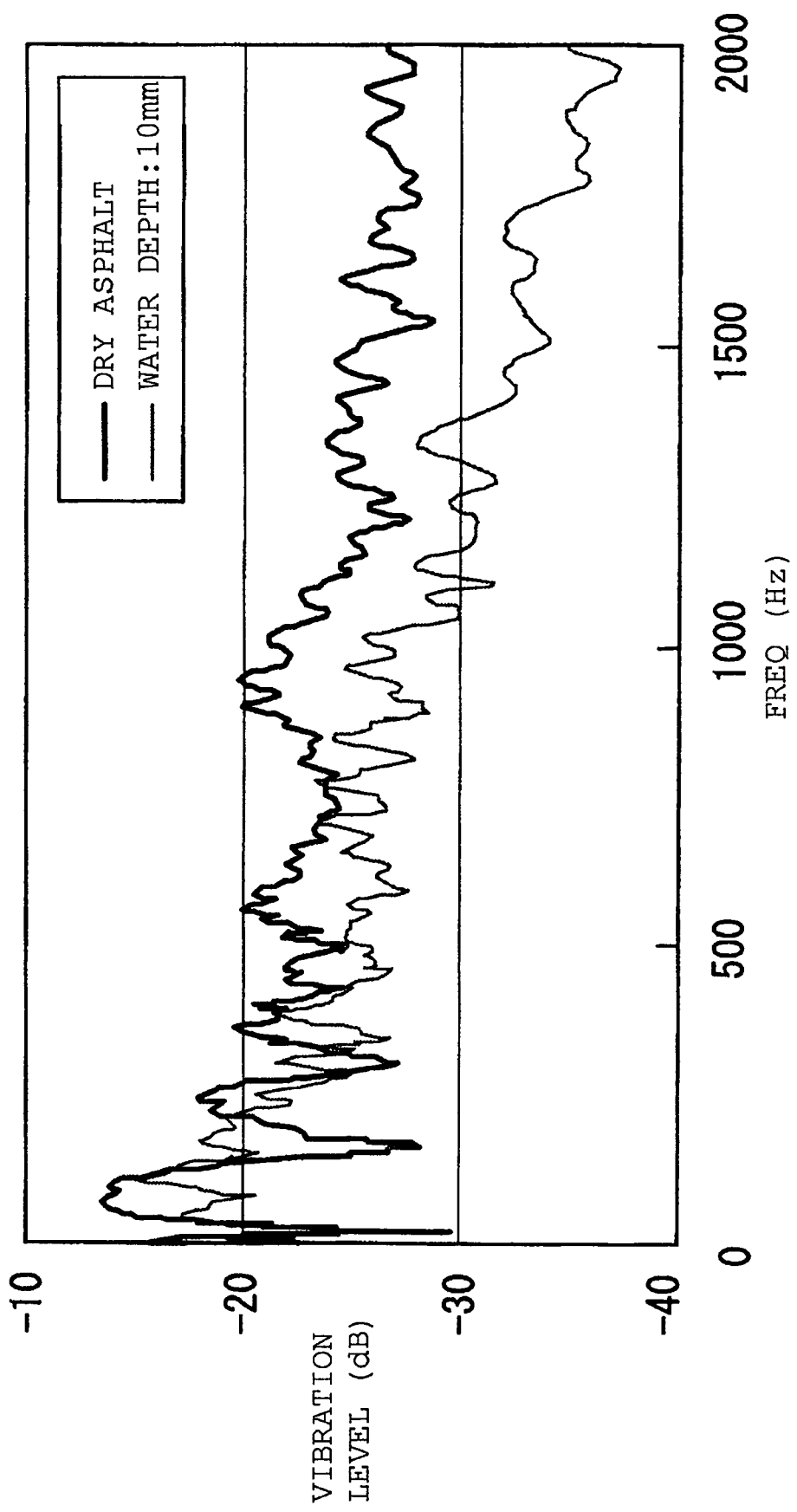
FIG. 9 is a graph showing a comparison between a frequency spectrum of a tire circumferential-direction vibration waveform of a vehicle running on a wet straight road and a frequency spectrum of a tire circumferential-direction vibration waveform of a vehicle running on a dry asphalt road.
Figure 10:
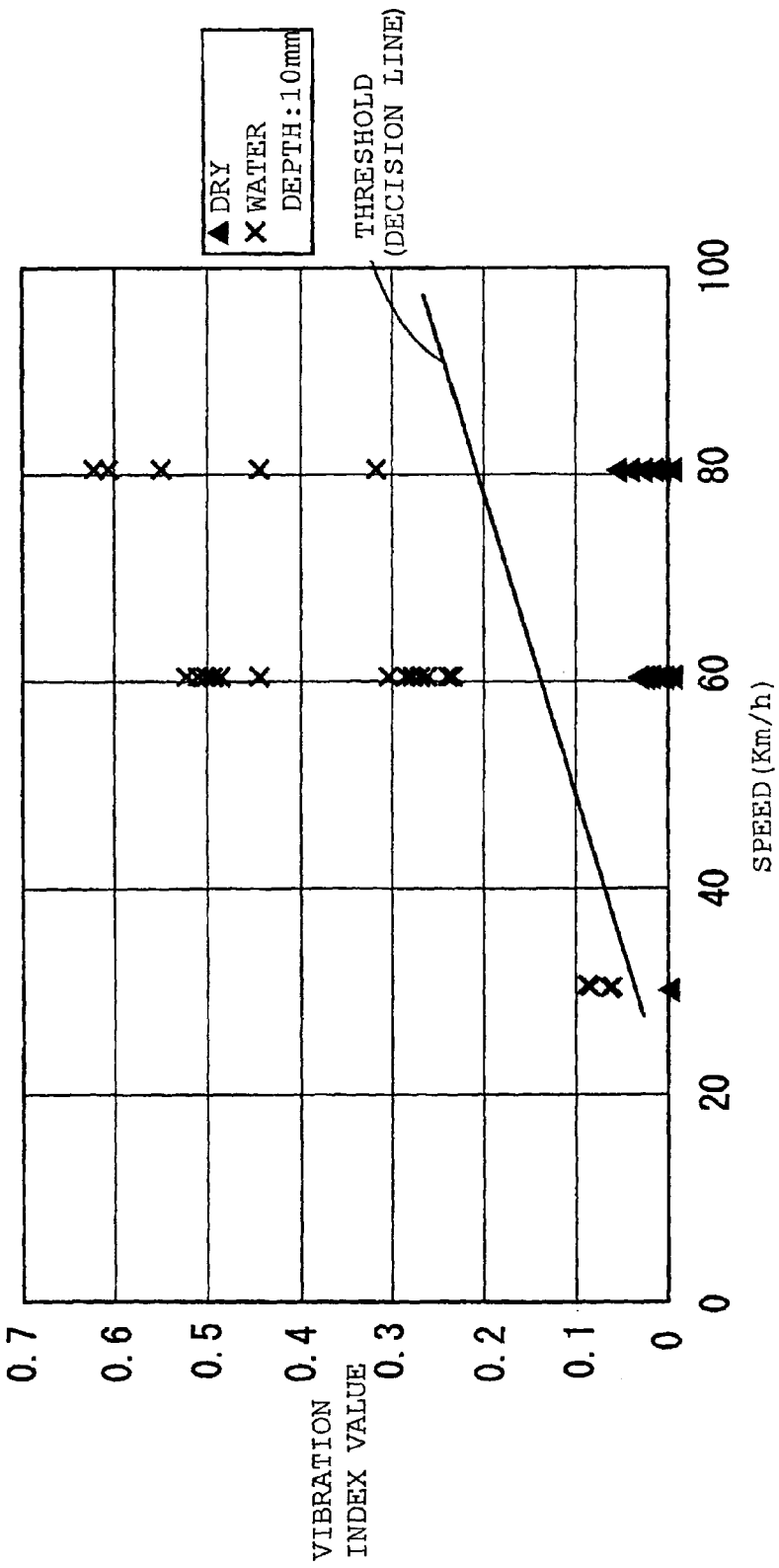
FIG. 10 is a graph showing a relationship between the ratio between vibration level in a pitch frequency band and speed and the vehicle speed.

FIG. 9 shows a comparison between an FFT frequency spectrum of the above-mentioned vibration waveform and an FFT frequency spectrum of a tire circumferential-direction vibration waveform measured with a vehicle driven on a dry asphalt road. It is clear from the figure that the vibration level rises near 1013 Hz, which is the tire pattern pitch frequency of the applicable speed of the vehicle used in the measurement. Since this frequency changes with vehicle speed, the vibration level of a frequency band including the above tire pattern pitch frequency was measured by changing the vehicle speed. The results are shown in FIG. 10, where the vibration index value represents the ratio between the vibration level in the pitch frequency band and the speed. It is evident that the vibration index value when the vehicle runs on a wet road is always larger than that when the vehicle runs on a dry asphalt road. Accordingly, it has been confirmed that with a proper decision line set in relation to the vehicle speed, it is possible to decide whether there is any matter, such as water or snow, lying on the road surface.

Embodiment 3

In Embodiment 2 heretofore described, the vibration level in a band which includes the pattern pitch frequency is used as an indicator of whether there is an intervening matter, such as water or snow, on a road surface. However, when the water depth is shallow or the like, the difference in vibration level between the wet road surface and the dry asphalt road surface becomes small, and as a result, decision errors are more likely to occur. In such a case, instead of the above-mentioned pattern pitch frequency, the vibration levels in a frequency band, whose lower-limit frequency is higher than the above-mentioned pattern pitch frequency and which also includes frequencies capable of increasing or decreasing with the vehicle speed in the same way as with the pattern pitch frequency, may be used as an indicator to reliably decide the presence or absence of an intervening matter on the road surface.

Figure 11:
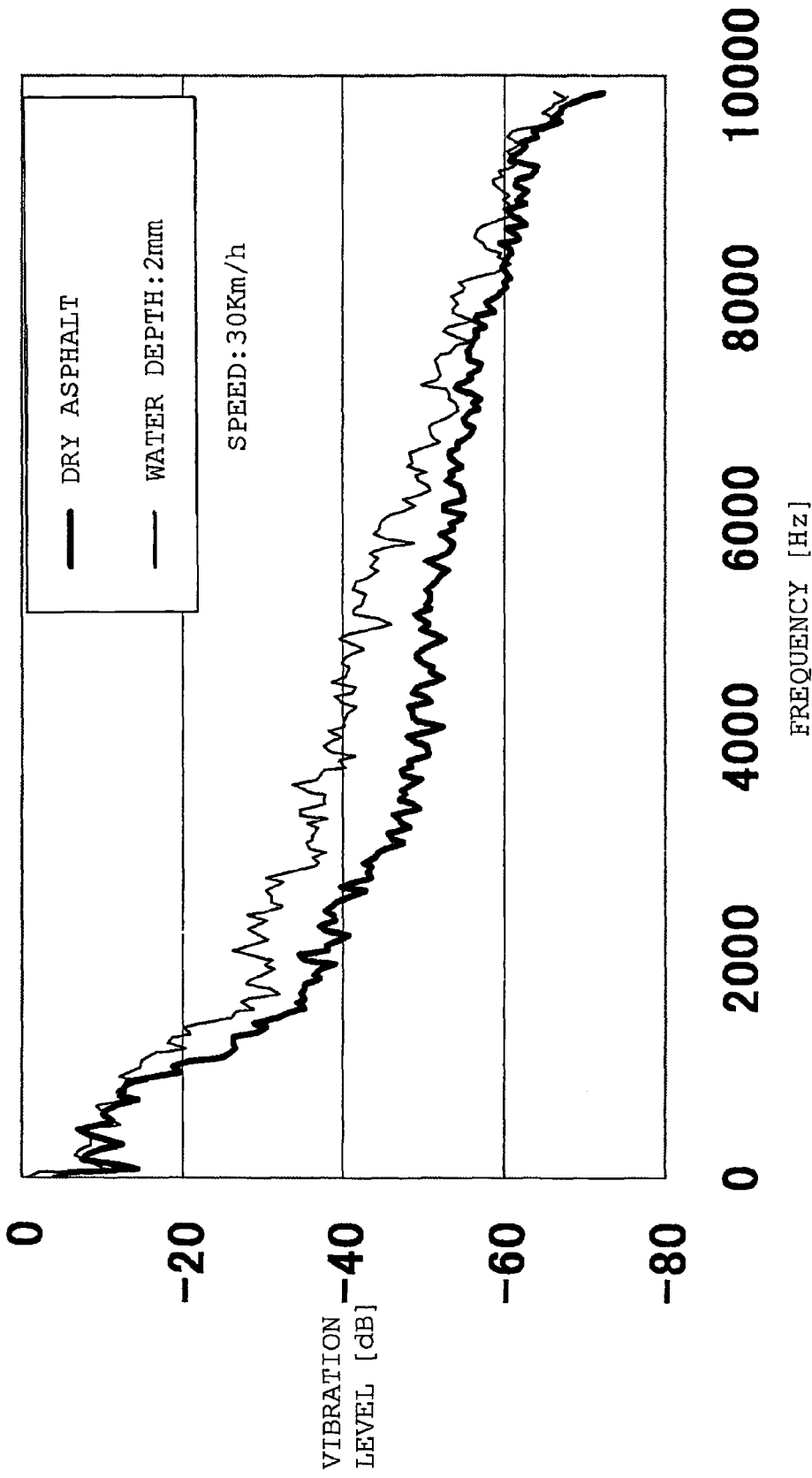
FIG. 11 is a graph showing a comparison between a frequency spectrum of a tire circumferential-direction vibration waveform of a vehicle running on a wet straight road with a shallow water depth and a frequency spectrum of a tire circumferential-direction vibration waveform of a vehicle running on a dry asphalt road (speed: 30 km/h).
Figure 12:
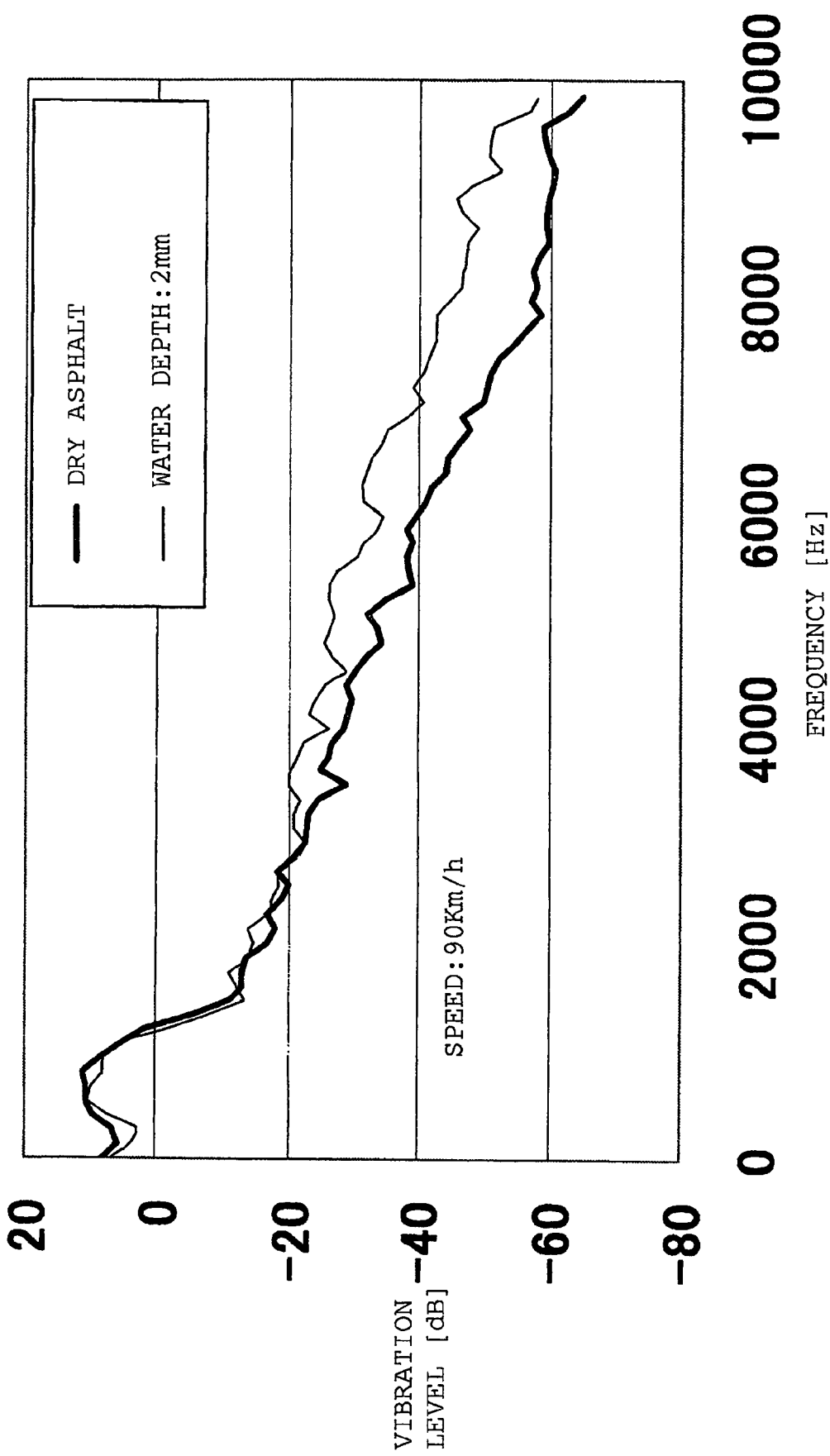
FIG. 12 is a graph showing a comparison between a frequency spectrum of a tire circumferential-direction vibration waveform of a vehicle running on a wet straight road with a shallow water depth and a frequency spectrum of a tire circumferential-direction vibration waveform of a vehicle running on a dry asphalt road (speed: 90 km/h).

FIG. 11 is frequency spectrums showing the results of an FFT analysis of tire vibration in the pre-leading domain extracted from the circumferential-direction vibration of tire measured with a vehicle fitted with a road surface condition estimating tire according to the present invention which was driven at 30 km/h on a wet straight road with a shallow water depth of 2 mm and a dry asphalt road, respectively. FIG. 12 shows the frequency spectrums when the vehicle speed was 90 km/h.

When the vehicle speed is 30 km/h, the pattern pitch frequency with this tire is a little below 1 kHz, but, unlike the case of deep water depth, there is only small difference between the vibration levels on the dry asphalt road indicated by a thick solid line in the figure and those on the wet road indicated by a fine solid line. In contrast to this, in the frequency band of 2 to 8 kHz, which is higher than the above-mentioned pattern pitch frequency, the vibration levels on the wet road surface rise, so that they exceed those on the dry asphalt road surface.

Also, when the vehicle speed is 90 km/h, the pattern pitch frequency shifts toward the higher-frequency side to about 3 kHz. However, in the frequency band including this 3 kHz, there is only small difference between the vibration levels on the dry asphalt road and those on the wet road. In contrast to this, in the frequency range higher than the pattern pitch frequency, more specifically, in the frequency band of 4 to 10 kHz, the vibration levels on the wet road are clearly higher than those on the dry asphalt road.

Therefore, when the vehicle speed is 30 km/h, it may be possible to reliably decide the presence or absence of an intervening matter as described above, even when the water depth is shallow, if the vibration level of a specific frequency, such as 4 kHz or 6 kHz, to be selected from a frequency range (2 to 8 kHz herein) higher than the pattern pitch frequency, which rises and drops with the vehicle speed, is calculated and the presence of a matter existing between road surface and tire is decided when the calculated vibration level exceeds a predetermined threshold value.

Also, a plurality of vibration levels in a specific frequency band, such as 3 to 6 kHz, from a frequency range higher than the pattern pitch frequency may be calculated, and the presence of an intervening matter between road surface and tire may be decided when the vibration level computed value calculated from the plurality of vibration levels exceeds a predetermined threshold value.

Also, when the vehicle speed is 90 km/h, a vibration level of a specific frequency, such as 5 kHz or 8 kHz, or a plurality of vibration levels in a specific frequency band, such as 5 to 8 kHz, may be calculated.

It is thus preferable that the specific frequency or a plurality of specific frequency bands for the decision as to whether there is any intervening matter between road surface and tire be changed according to the vehicle speed and at the same time the threshold value for the decision on the presence of an intervening matter be also changed according to the vehicle speed or the tire type.

Embodiment 4

In Embodiments 1, 2 and 3 heretofore described, the presence or absence of an intervening matter existing between road surface and tire is estimated using data of vibration in the pre-trailing domain from the time-series waveform of tire vibration. However, as stated already, the vibration levels in a relatively low frequency band, out of the vibration levels in the post-trailing domain, display a low degree of temperature dependence (less changing with temperature). And therefore the vibration levels in the pre-trailing domain and the vibration levels in the relatively low frequency band out of the vibration levels in the post-trailing domain may be used to estimate a road surface condition. This may not only realize an estimation of a road surface condition with accuracy but also improve the robustness of the system against temperature disturbance.

Figure 13:
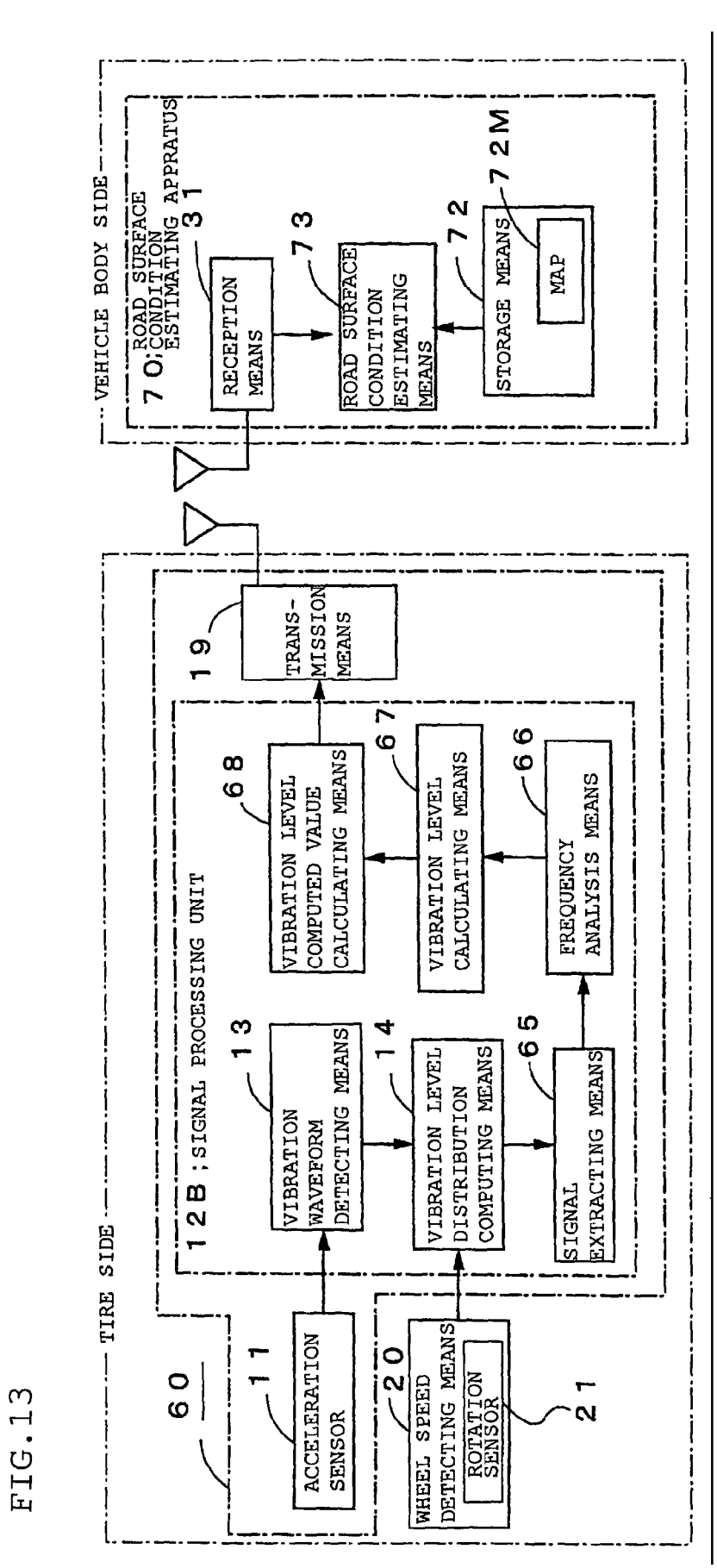
FIG. 13 is a function block diagram showing a structure of a road surface condition estimating system according to Embodiment 4.

FIG. 13 is a function block diagram showing a structure of a road surface condition estimating system according to Embodiment 4, in which the same reference numbers are used to indicate the same parts as in Embodiment 1. In FIG. 13, 60 is a road surface condition estimating tire, which comprises an acceleration sensor 11 as a vibration detecting means for detecting vibration inputted to the tire, a signal processing unit 12B for calculating computed values of vibration levels of tire vibration by processing the output signals of the acceleration sensor 11, and a transmission means 19 for transmitting the data of the calculated computed values of vibration levels to the vehicle body side; and 20 is a wheel speed detecting means, equipped with a rotation sensor 21, for detecting the rotation speed of the wheel. Also, 70 is a road surface condition estimating apparatus, which is provided with a reception means 31 for receiving data of vibration level computed values transmitted from the transmission means 19, a storage means 72 for storing a map 72M showing a previously determined relationship between road surface conditions and the vibration level computed value, and a road surface condition estimating means 73 for estimating the condition of a road surface on which the vehicle is running, based on the received data of the vibration level computed value and the map 72M, and thereby estimates a road surface condition based on the vibration level computed value transmitted from the road surface condition estimating tire 60. And this road surface condition estimating apparatus 70 is installed on the vehicle body side.

The signal processing unit 12B, to be specific, is provided with a vibration waveform detecting means 13 for obtaining a vibration waveform by arranging in a time series the vibration inputted to a road surface condition estimating tire ("tire" in the following) 60 of a running vehicle, which is the output of the acceleration sensor 11, a vibration level distribution computing means 14 for obtaining a distribution of vibration levels by converting the vibration waveform into vibration waveforms corresponding to predetermined positions of the tire by using output pulses from the rotation sensor 21, a signal extracting means 65 for identifying an accurate trailing edge position of the tire 60 from a peak position of the tire vibration that appears in the vicinity of a tire contact patch and at the same time dividing data of the vibration level distribution into data in two domains, namely, the pre-trailing domain and the post-trailing domain, and extracting the respective data of vibration levels in the above-mentioned domains, a frequency analysis means 66, such as an FFT analyzer, for performing a frequency analysis on the thus extracted time-series waveforms of the respective vibration levels, a vibration level calculating means 67 for calculating vibration levels in a predetermined frequency band of the frequency spectrums in the respective domains obtained by the frequency analysis means 66, a vibration level computed value calculating means 68 for calculating the computed values of vibration levels by using the calculated vibration levels in the respective domains, and a transmission means 19 for transmitting the data of the calculated computed values of vibration levels to the vehicle body side.

Note that an acceleration sensor 11 and the positions of placement of the acceleration sensor 11 and the signal processing unit 12B as used in this embodiment are the same as those of Embodiments 1 and 2. Also, in this embodiment, too, the detecting direction of the acceleration sensor 11 is arranged to be the tire circumferential direction, so that the tire circumferential-direction vibration inputted from the road surface is detected.

Next, a description will be given of a method for estimating a road surface condition according to Embodiment 4.

Firstly, an acceleration sensor 11 detects the circumferential-direction vibration of a tire 60 of a running vehicle and sends the output to a vibration waveform detecting means 13, where a vibration waveform in the tire circumferential direction arranged in a time series, as shown in FIGS. 5A and 5B, is obtained. Then a vibration level distribution computing means 14 processes the vibration waveform and thereby establishes correspondence of a leading edge position and a trailing edge position to the time axis of the vibration waveform arranged in a time series. The steps thus far are the same as those of Embodiment 1.

Figure 14:
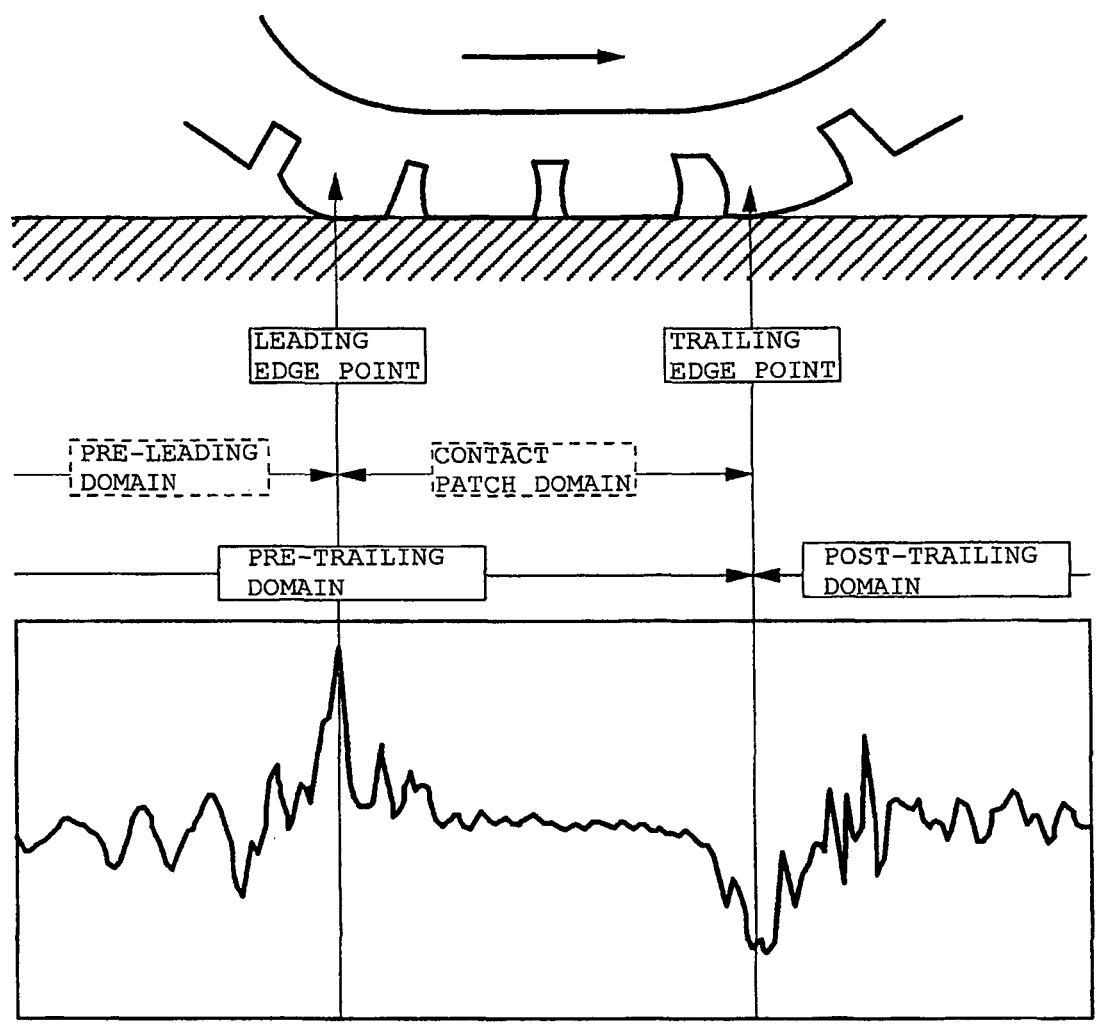
FIG. 14 is an illustration showing the pre-leading domain, the contact patch domain, and the post-trailing domain of a tire vibration waveform.

In the present example, as shown in FIG. 14, the data of vibration level distribution, which is the vibration waveform arranged in a time series, are divided into those of the pre-leading domain and the contact patch domain or into those of the domain covering the pre-leading domain and the contact patch domain (pre-trailing domain) and the post-trailing domain. Note that, in this embodiment, too, a trailing edge position is first identified and then a leading edge position is identified therefrom.

Next, a signal extracting means 65 extracts a time-series waveform in the pre-trailing domain, according to the above division, and a time-series waveform in the post-trailing domain, respectively. Then the data of the extracted time-series waveforms in the respective domains are sent to a frequency analysis means 66, where a frequency spectrum in the pre-trailing domain and a frequency spectrum in the post-trailing domain are obtained by a frequency analysis.

Figure 15:
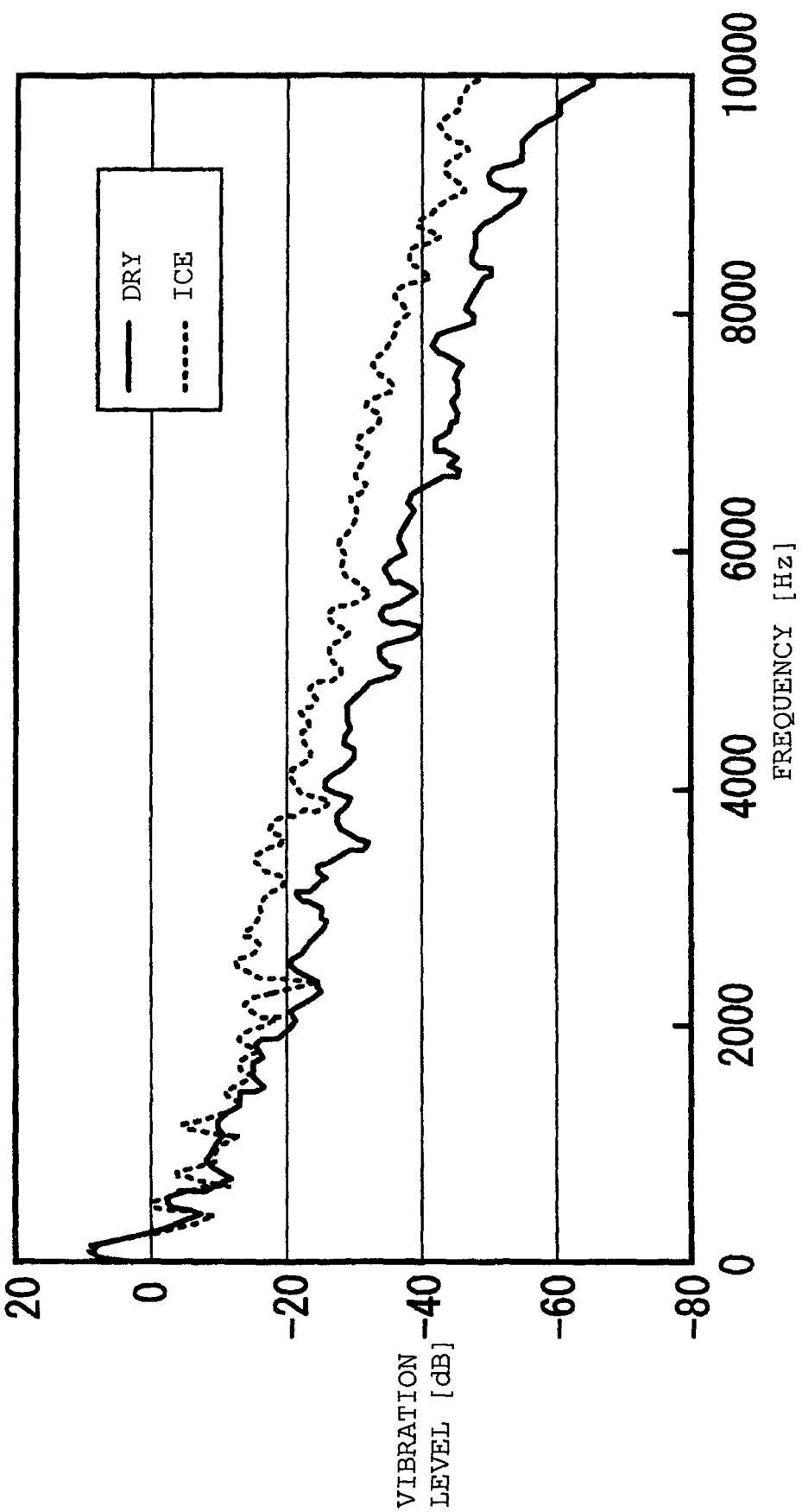
FIG. 15 is a graph showing FFT waveforms in the pre-trailing domain.

FIG. 15 shows a comparison of the frequency spectrums (FFT waveforms) in the pre-trailing domain of tire vibration in the circumferential direction, between one on a dry asphalt road as shown in FIG. 5A and one on an ice-covered road as shown in FIG. 5B. It can be seen that in the pre-trailing domain, the vibration levels on the dry asphalt road are generally lower than those on the ice-covered road, and the difference therebetween is larger in the frequency band of 2 to 10 kHz, especially 8 to 10 kHz.

Figure 16:
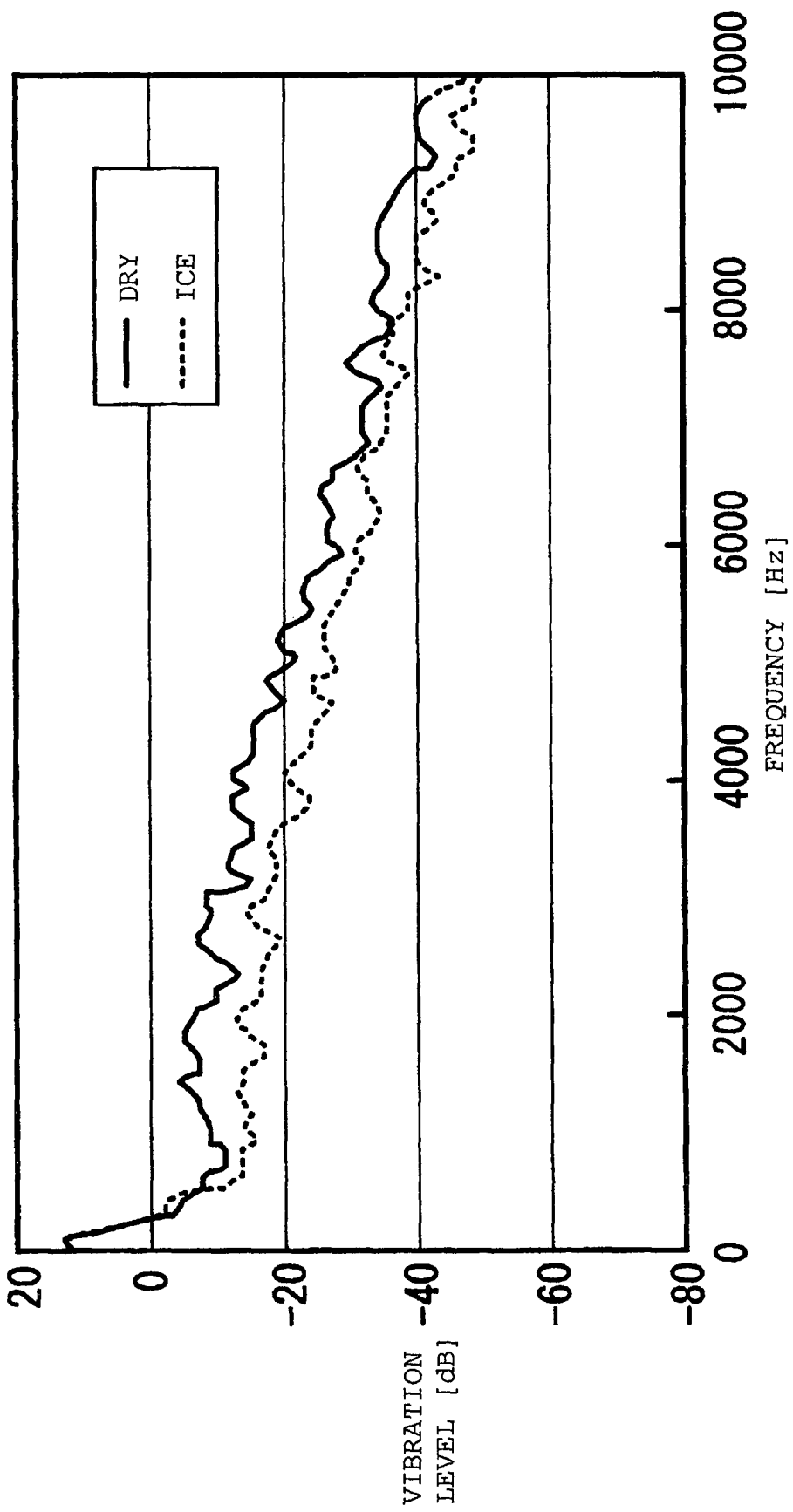
FIG. 16 is a graph showing FFT waveforms in the post-trailing domain.

FIG. 16 shows a comparison of the frequency spectrums (FFT waveforms) in the post-trailing domain of tire vibration in the circumferential direction, between one on a dry asphalt road as shown in FIG. 5A and one on an ice-covered road as shown in FIG. 5B. It can be seen that in the post-trailing domain, in contrast to the case of the pre-trailing domain, the vibration levels on the ice-covered road are generally lower than those on the dry asphalt road, and the difference therebetween is larger in the frequency band of 0.5 to 4 kHz, especially 1 to 3 kHz.

Thereupon, a vibration level in the frequency band of 8 to 10 kHz (pre-trailing vibration level) is calculated from the frequency spectrum in the pre-trailing domain, and at the same time a vibration level in the frequency band of 1 to 3 kHz (post-trailing vibration level) is calculated from the frequency spectrum in the post-trailing domain. Then a ratio of the pre-trailing vibration level to the post-trailing vibration level is obtained to use it as a vibration level computed value S. As mentioned above, the post-trailing vibration level on the dry asphalt road is higher than the post-trailing vibration level on the ice-covered road, and on the contrary, the pre-trailing vibration level on the dry asphalt road is lower than the pre-trailing vibration level on the ice-covered road. Hence, a road surface condition may be estimated with accuracy if the above-mentioned vibration level computed value S is used in the estimation.

In the present embodiment, a vibration level calculating means 67 calculates a pre-trailing vibration level and post-trailing vibration level as mentioned above, respectively, and sends the results to a vibration level computed value calculating means 68. The vibration level computed value calculating means 68 obtains a ratio of the pre-trailing vibration level to the post-trailing vibration level to use it as a vibration level computed value S and transmits the vibration level computed value S via the transmission means 19 to a road surface condition estimating apparatus 37 provided on the vehicle body side.

At the road surface condition estimating apparatus 70, a reception means 31 receives the data of the vibration level computed value, and a road surface condition estimating means 73 estimates the condition of a road surface on which the vehicle is running, based on the vibration level computed value S and a map 72M stored in a storage means 72, which shows a relationship between previously obtained road surface conditions and vibration level computed values S of tire vibration.

In this manner, the condition of a road surface on which a vehicle is running can be estimated with accuracy. Also, since the vibration level in the frequency band of 8 to 10 kHz in the pre-trailing domain and the vibration level in the frequency band of 1 to 3 kHz in the post-trailing domain are both less affected by the influence of temperatures, the robustness against temperature disturbance is also improved.

Note also that if a map showing a relationship between the vibration level computed value S and the road surface friction coefficient μ, instead of the map 72M, is prepared, the road surface friction coefficient μ can also be estimated with accuracy.

Thus, according to the present Embodiment 4, the tire vibration in the circumferential direction of a tire 60 of a running vehicle is detected by the tire 69, fitted with an acceleration sensor 11 and a signal processing unit 12B for signal-processing the output of the acceleration sensor 11 and transmitting the result to the vehicle body side. Then after an exact trailing edge position of the tire 10 is identified from the vibration waveform, the time-series waveform of the vibration is divided into that in the pre-trailing domain and that in the post-trailing domain, which are then subjected to a frequency analysis. Then a vibration level in the 8 to 10 kHz range of the thus obtained frequency spectrum in the pre-trailing domain and a vibration level in the 1 to 3 kHz range of the frequency spectrum in the post-trailing domain are calculated, and a vibration level computed value S is obtained from the thus calculated pre-trailing vibration level and post-trailing vibration level. And the vibration level computed value S is transmitted to a road surface condition estimating apparatus 70 provided on the vehicle body side. Now on the vehicle body side, the condition of a road surface on which the vehicle is running is estimated, based on the received vibration level computed value S and a map 72M stored in a storage means 72, which shows a relationship between vibration level computed values S and previously obtained road surface conditions. Therefore, a road surface condition can be estimated with accuracy.

Also, in the present embodiment, the vibration levels used for the estimation of a road surface condition are the vibration level in 1 to 3 kHz in the post-trailing domain and the vibration level in 8 to 10 kHz in the pre-trailing domain, which are less affected by the influence of temperatures, so that the robustness against temperature disturbance can be improved.

In Embodiment 4 as described above, a road surface condition is estimated using a vibration level computed value S, which is a ratio between a vibration level in the frequency band of 1 to 3 kHz (post-trailing vibration level) in the post-trailing domain and a vibration level in the frequency band of 8 to 10 kHz (pre-trailing vibration level) in the pre-trailing domain. However, as shown in FIG. 15 and FIG. 16, the pre-trailing vibration level and the post-trailing vibration level both show significant difference between the vibration level on a dry asphalt road and the vibration level on an ice-covered road. Therefore, if a previously obtained map showing a relationship between the pre-trailing vibration level and the road surface condition or between the post-trailing vibration level and the road surface condition is prepared, it is possible to estimate a road surface condition with only the data of the pre-trailing vibration level or the data of the post-trailing vibration level.

Also, in the present embodiment, tire vibration in the circumferential direction detected at the width center of a tire tread 10a by an acceleration sensor 11. However, the direction of vibration detection by the acceleration sensor 11 may be the width direction of a tire; that is, the vibration at the tread edge, which develops a deformation opposite to one near the tread center, may be detected also and thus the vibration in the tire width direction may be detected.

Also, on an ice-covered road surface, where variation in the data of vibration levels is wide, it is preferable that a plurality of acceleration sensors 11 be arranged on the tire circumference and an average value of vibration level computed values obtained by the plurality of the sensors be used for the estimation of a road surface condition. This way, the estimation accuracy of a road surface condition may be further improved.

Also, in the above-described embodiment, the frequency band in the post-trailing domain is 1 to 3 kHz, and the frequency band in the pre-trailing domain is 8 to 10 kHz, but the present invention is not limited thereto. Those frequency bands may be set as appropriate, according to tire type, vehicle speed, or the like.

Note also that the frequency band in the post-trailing domain may be any frequency band as long as it is selected from within the frequency band of 0.5 to 4 kHz and that the frequency band in the pre-trailing domain may be any frequency band selected from within the frequency band of 2 to 10 kHz.

Also, in the above-described embodiment, a frequency analysis is performed by a frequency analysis means 66 on the time-series waveforms of vibration in the respective domains to obtain their respective frequency spectrums. And from the respective frequency spectrums, a vibration level in the frequency band of 1 to 3 kHz (post-trailing vibration level) in the post-trailing domain and a vibration level in the frequency band of 8 to 10 kHz (pre-trailing vibration level) in the pre-trailing domain are calculated. However, it may be so arranged that instead of the frequency analysis means 66, a band-pass filter may be used to extract a time-series waveform of 1 to 3 kHz in the post-trailing domain and a time-series waveform of 8 to 10 kHz in the pre-trailing domain, respectively, and the pre-trailing vibration level and the post-trailing vibration level may be calculated.

Also, in the above-described embodiment, a road surface condition is estimated using a map 72M which shows a previously determined relationship between the vibration level computed value S of tire vibration and road surface conditions. However, instead of using the map 72M, a threshold value K may be established for the vibration level computed value S, and a decision may be made such that the road surface is a high $\mu$ road surface when the vibration level computed value is at or below the threshold value K and it is a low $\mu$ road surface when the vibration level computed value is above the threshold value K. Or threshold values K1 and K2 may be established, and a decision may be made such that the road surface is a high $\mu$ road surface when S≤K1, a medium $\mu$ road surface when K1<S≤K2, or a low $\mu$ road surface when K2<S. In such a case, the threshold value K may be changes as appropriate according to tire type, vehicle speed or the like, so that the accuracy of estimation of a road surface condition may be further improved.

In Embodiments 1 to 4 heretofore described, the condition of a road surface on which one's own vehicle is running is estimated. However, if a road surface condition estimation apparatus 30, 50, or 70 is provided with a means for wirelessly transmitting the information on the estimated road surface condition to the other vehicles, then it is possible to communicate a road surface condition ahead to the vehicles running behind on the same road. Also, if a vehicle running behind is provided with a means for receiving the wirelessly transmitted information on a road surface condition and a means for grasping the road surface condition ahead from the information on the road surface condition transmitted from a vehicle running ahead, the vehicle running behind can easily grasp a road surface condition ahead.

Furthermore, if the above-mentioned vehicle is provided not only with a road surface condition estimating tire 10, a wheel speed detecting means 20, a road surface condition estimating apparatus 30 or 70 but also with a means for estimating the distance to a vehicle ahead and a vehicle running control means for controlling the running condition of a vehicle based on the road surface information from the means for grasping the road surface condition ahead, the inter-vehicular distance information from the inter-vehicular distance estimating means, and the wheel speed information from the wheel speed detecting means, then it is possible to control the running condition of a vehicle based on not only the information on the condition of a road surface on which the vehicle is running, but also the information on a road surface condition ahead and the information on the distance to a vehicle running ahead. As a result, the safety of vehicular running will be greatly enhanced.

EXAMPLE 3

Figure 17:
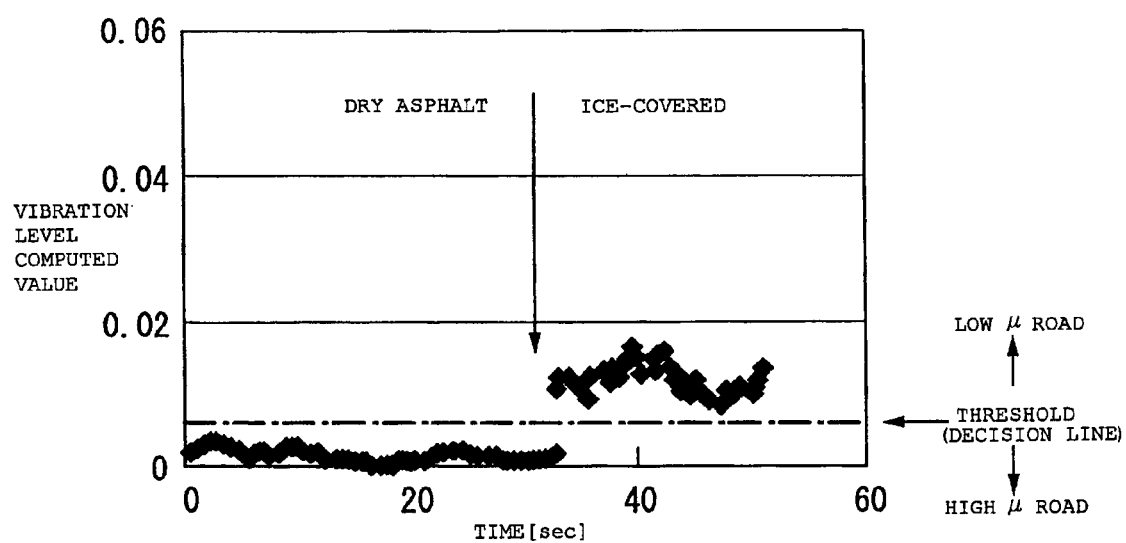
FIG. 17 is a diagram showing changes of vibration level computed value when a vehicle is driven at a constant speed from a dry asphalt road onto an ice-covered road.

A vehicle fitted with a road surface condition estimating tire according to the present invention was driven at a constant speed from a dry asphalt road surface ($\mu \approx 1$) onto an ice-covered road surface ($\mu \approx 0.1$), and the change of the vibration level computed value with time was measured. The results are shown in FIG. 17. The horizontal axis of the figure represents time, and the vertical axis the vibration level computed value, which is the ratio between the pre-trailing vibration level and the post-trailing vibration level. The decision line in the figure is a predetermined value intermediate between the bottom value of the vibration level computed value on an ice-covered road and the top value thereof on a dry asphalt road. And the road surface is decided to be a low $\mu$ road when the vibration level computed value is above the decision line and a high $\mu$ road when it is below the decision line As is evident from the figure, the vibration level computed value increases simultaneously as the vehicle enters on the ice-covered road surface, and we can see that the vehicle has entered on a low $\mu$ road from a high $\mu$ road. Thus it has been confirmed that the slipperiness of a road surface can be decided by setting a proper threshold value.

INDUSTRIAL APPLICABILITY

As discussed herein, according to the present invention, a road surface condition may be estimated from tire behavior with robustness against temperatures or vehicle speeds even during a normal running of a vehicle. Therefore, the accuracy of vehicle control, such as ABS or VSC, can be enhanced markedly by the use of information on a road surface condition as described above.

The invention claimed is:

1. A road surface condition estimating apparatus comprising:
a reception means for receiving the wirelessly transmitted data of a vibration level or a vibration level computed value from a road surface condition estimating tire; and
a road surface condition estimating means for estimating a road surface condition based on the vibration level or the vibration level computed value; and
the road surface condition estimating tire comprising:
a tire vibration detecting means disposed on the air chamber side of an inner liner in a tire tread area, the tire vibration detecting means detecting the vibration of a tire of a running vehicle;
a pre-trailing domain signal extracting means for extracting signals of the pre-trailing domain, which is a domain before a trailing position estimated from a peak position of said tire vibration detected by said tire vibration detecting means;
a post-trailing domain signal extracting means for extracting signals of tire vibration in the post-trailing domain, which is a domain after the trailing position estimated from the peak position of said tire vibration detected by said tire vibration detecting means;
a frequency analysis means for analyzing the frequencies of said signals extracted by the pre-trailing domain signal extracting means and signals extracted by the post-trailing domain signal extracting means and obtaining a frequency spectrum in the pre-trailing domain and a frequency spectrum in the post-trailing domain;
a vibration level calculating means for calculating a vibration level of a frequency band, the lower-limit frequency of which being 0.5 kHz or above and the upper-limit frequency of which being 4 kHz or below, from the obtained frequency spectrum of the post-trailing domain obtained by the frequency analysis means, and a vibration level of a frequency band, the lower-limit frequency of which being 2 kHz or above and the upper-limit frequency of which being 10 kHz or below, from a frequency spectrum of the pre-trailing domain obtained thereby;
a means for calculating a vibration level computed value using said calculated vibration level in the post-trailing domain and vibration level in the pre-trailing domain;
a means for wirelessly and automatically transmitting data of the vibration level or vibration level computed value to the vehicle body side; and
a transmission means for wirelessly and automatically transmitting information of the estimated road surface condition to another vehicle automatically,
wherein the frequency band for calculating the vibration level is higher in pre-trailing domain than the band in the post-trailing domain.

2. A road surface condition estimating apparatus comprising:
a reception means for receiving the wirelessly transmitted data of vibration level or vibration level computed value from a road surface condition estimating tire; and
a road surface condition estimating means for estimating a road surface condition based on the vibration level or the vibration level computed value; and
the road surface condition estimating tire comprising:
a tire vibration detecting means disposed on the air chamber side of an inner liner in a tire tread area, said tire vibration detecting means detecting the vibration of a tire of a running vehicle;
a pre-trailing domain signal extracting means for extracting signals of a pre-trailing domain, which is a domain before the trailing position estimated from a peak position of said tire vibration detected by said tire vibration detecting means;
a post-trailing domain signal extracting means for extracting signals tire vibration in the post-trailing domain, which is a domain after the trailing position estimated from the peak position of said tire vibration detected by said tire vibration detecting means;
a band-pass filter for extracting a signal in the post-trailing domain, whose lower-limit frequency of which being 0.5 kHz or above and upper-limit frequency of which being 4 kHz or below out of the signal in the post-trailing domain, and a signal in the pre-trailing domain, whose lower-limit frequency of which being 2 kHz or above and upper-limit frequency of which being 10 kHz or below out of the signal in the pre-trailing domain by inputting said signals of the post-trailing domain extracted by the post-trailing domain signal extracting means and signals of the pre-trailing domain extracted by the pre-trailing domain signal extracting means;
a vibration level calculating means for calculating a vibration level which is the vibration level of the signal in the post-trailing domain and a vibration level which is the vibration level of the signal in the pre-trailing domain, which are extracted by the band-pass filter;
a means for calculating a vibration level computed value using said calculated vibration level in the post-trailing domain and vibration level in the pre-trailing domain; and a means for wirelessly and automatically transmitting data of the vibration level or vibration level computed value to the vehicle body side; and a transmission means for wirelessly and automatically transmitting information of the estimated road surface condition to another vehicle, wherein the frequency band for calculating the vibration level is higher in pre-trailing domain than the band in the post-trailing domain.

3. The road surface condition estimating apparatus according to claim 1 or 2, further comprising: a reception means for automatically receiving the wirelessly transmitted information on a road surface condition; and a means for automatically grasping a road surface condition ahead from information on a road surface condition automatically transmitted from a vehicle running ahead.

* * * * *